US007996155B2

(12) United States Patent
Weng

(10) Patent No.: US 7,996,155 B2
(45) Date of Patent: Aug. 9, 2011

(54) ANOVA METHOD FOR DATA ANALYSIS

(75) Inventor: Lee Weng, Bellevue, WA (US)

(73) Assignee: Microsoft Corporation, Redmond, WA (US)

( * ) Notice: Subject to any disclaimer, the term of this patent is extended or adjusted under 35 U.S.C. 154(b) by 1629 days.

(21) Appl. No.: 10/349,364

(22) Filed: Jan. 22, 2003

(65) Prior Publication Data

US 2004/0143399 A1 Jul. 22, 2004

(51) Int. Cl.
*G01N 33/48* (2006.01)
*G01N 31/00* (2006.01)
*G06G 7/48* (2006.01)
(52) U.S. Cl. ............................... 702/19; 702/22; 703/11
(58) Field of Classification Search .................. None
See application file for complete search history.

(56) References Cited

U.S. PATENT DOCUMENTS

| 5,265,617 | A | 11/1993 | Verrier et al. |
| 5,510,270 | A | 4/1996 | Fodor et al. |
| 5,539,083 | A | 7/1996 | Cook et al. |
| 5,545,522 | A | 8/1996 | Van Gelder et al. |
| 5,556,752 | A | 9/1996 | Lockhart et al. |
| 5,569,588 | A | 10/1996 | Ashby et al. |
| 5,578,832 | A | 11/1996 | Trulson et al. |
| 5,716,785 | A | 2/1998 | Van Gelder et al. |
| 5,842,997 | A | 12/1998 | Verrier et al. |
| 5,891,636 | A | 4/1999 | Van Gelder et al. |
| 6,028,189 | A | 2/2000 | Blanchard |
| 6,040,138 | A | 3/2000 | Lockhart et al. |
| 6,132,997 | A | 10/2000 | Shannon |
| 6,218,122 | B1 | 4/2001 | Friend et al. |
| 6,243,615 | B1 | 6/2001 | Neway et al. |
| 6,271,002 | B1 | 8/2001 | Linsley et al. |
| 6,351,712 | B1 | 2/2002 | Stoughton et al. |
| 6,713,257 | B2 | 3/2004 | Shoemaker et al. |
| 2001/0034023 | A1 | 10/2001 | Stanton, Jr. et al. |
| 2003/0226098 | A1 | 12/2003 | Weng |

FOREIGN PATENT DOCUMENTS

| EP | 0 534 858 | 9/1992 |
| WO | WO 90/11364 | 10/1990 |
| WO | WO 98/38329 | 9/1998 |
| WO | WO 98/41531 | 9/1998 |
| WO | WO 99/58708 | 11/1999 |
| WO | WO 99/59037 | 11/1999 |
| WO | WO 99/66067 | 12/1999 |
| WO | WO 00/24936 | 5/2000 |
| WO | WO 00/39336 | 7/2000 |
| WO | WO 01/05935 | 1/2001 |
| WO | WO 02/16650 | 2/2002 |
| WO | WO 02/44399 | 6/2002 |

OTHER PUBLICATIONS

Choueiki et al., "Training Data Development with the D-Optimality Criterion" (1999) vol. 10, No. 1, pp. 56-63.*
Ramsey "Sampling as a source of measurement uncertainty: techniques for quantification and comparison with analystical sources" JAAS (1998) vol. 13, pp. 97-104.*
Michelson et al. "The Biostatistics Cookbook" Kluwer Academic Publishers (1996), pp. 14-27.*
Bass, 2000, "Double-stranded RNA as a template for gene silencing", Cell (101):235-238.
Belshaw et al., 1996, "Controlling protein association and subcellular localization with a synthetic ligand that induces heterodimerization of proteins", Proc Natl Acad Sci USA (93):4604-4607.
Blanchard et al., 1998, "Synthetic DNA Arrays", Genetic Engineering (Setlow JK): 111-123.
Blanchard et al., 1996, "Sequence to array: probing the genome's secrets", Nat Biotechnol (14):1649.
Blanchard et al., 1996, "High-density oligonucleotide arrays", Biosensors & Bioelectronics (11):687-690.
Chech, 1987, "The chemistry of self-splicing RNA and RNA enzymes", Science (236):1532-1539.
Chirgwin et al., 1979, "Isolation of biologically active ribonucleic acid from sources enriched in ribonuclease", Biochemistry (18):5294-5299.
Crollius et al., 2000, "Estimate of human gene number provided by genomewide analysis using *Tetraodon nigroviridis* DNA sequence", Nat Genet (25):235-238.
de Wildt et al., 2000, "Antibody arrays for high-throughput screening of antibody-antigen interactions", Nat Biotechnol (18):989-994.
DeRisi et al., 1996, "Use of a cDNA microarray to analyse gene expression patterns in human cancer", Nat Genet (14):457-460.
Dohmen et al., 1994, "Heat-inducible degron: a method for constructing temperature-sensitive mutants", Science (263):1273-1276.
Duggan et al., 1999, "Expression profiling using cDNA microarrays", Nat Genet (21):10-14.
Egholm et al., 1993, "PNA hybridizes to complementary oligonucleotides obeying the Watson-Crick hydrogen-bonding rules," Nature (365):566-568.
Elbashir et al., 2001, "Duplexes of 21-nucleotide RNAs mediate RNA interference in cultured mammalian cells", Nature (411):494-498.
Ewing et al., 2000, "Analysis of expressed sequence tags indicates 35", Nat Genet (25):232-234.
Ferguson et al., 1996, "A fiber-optic DNA biosensor microarray for the analysis of gene expression", Nat Biotechnol (14):1681-1684.
Fire et al., 1998, "Potent and specific genetic interference by double-stranded RNA in Caenorhabditis elegans", Nature (391):806-811.
Fodor et al., 1991, "Light-directed, spatially addressable parallel chemical synthesis", Science (251):767-773.
Froehler et al., 1986, "Synthesis of DNA via deoxynucleoside H-phosphonate intermediates", Nucleic Acids Res (14):5399-5407.
Gibson I, 1996, "Antisense approaches to the gene therapy of cancer—'Recnac'", Cancer Metastasis Rev (15):287-299.

(Continued)

*Primary Examiner* — Eric S Dejong
(74) *Attorney, Agent, or Firm* — Klarquist Sparkman LLP

(57) ABSTRACT

The present invention provides improved ANOVA methods for analyzing measured data and transformed data. The improved ANOVA method takes two data types as its input, one is the measurements, the other is a predetermined error associated with the measurements. The latter can come from a technology/platform-specific error model. Because of the additional input information, the statistical power is increased. The methods of the invention is particularly useful for analyzing gene or protein expression data.

18 Claims, 2 Drawing Sheets

OTHER PUBLICATIONS

Figure 1:
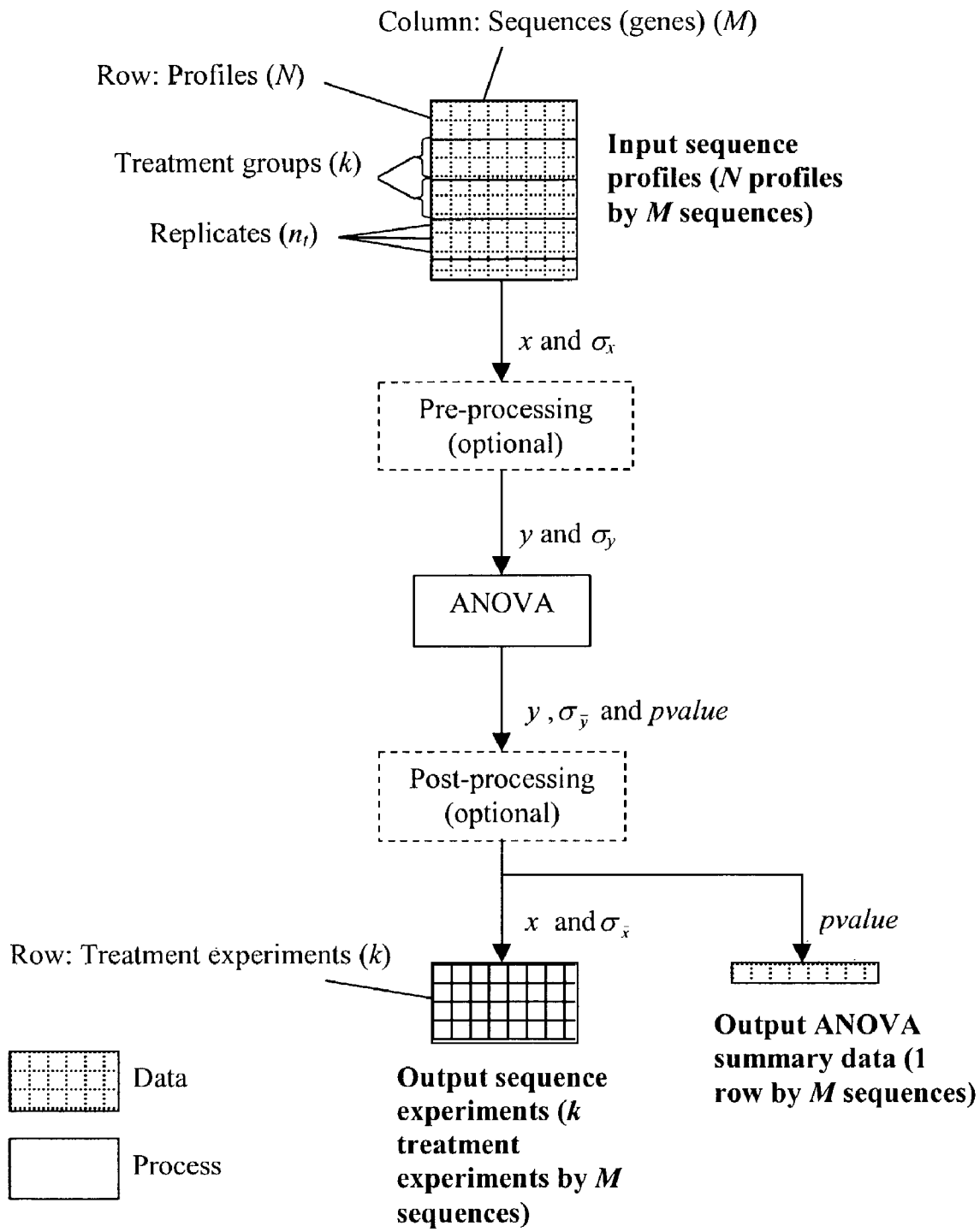

Goffeau et al., 1996, "Life with 6000 genes", Science (274):546-567.
Good et al., 1997, "Expression of small therapeutic RNAs in human cell nuclei", Gene Ther (4):45-54.
Gossen et al., 1992, "Tight control of gene expression in mammalian cells by tetracycline-responsive promoters", Proc Natl Acad Aci U S A (89):5547-5551.
Grant SR, 1999, "Dissecting the mechanisms of posttranscriptional gene silencing: divide and conquer", Cell (96):303-306.
Grassi et al., 1996, "Ribozymes: structure function and potential therapy for dominant genetic disorders", Ann Med (28):499-510.
Guo et al., 1995, "par-1, a gene required for establishing polarity in C. elegans embryos, encodes a putative Ser/Thr kinase that is asymmetrically distributed", Cell (81):611-620.
Gygi et al., 1999, "Quantitative analysis of complex protein mixtures using isotope-coded affinity tags", Nat Biotechnol (17):994-999.
Haseloff et al., 1988, "Simple RNA enzymes with new and highly specific endoribonuclease activities", Nature (334):585-591.
Hoffmann et al., 1997, "A novel tetracycline-dependent expression vector with low basal expression and potent regulatory properties in various mammalian cell lines", Nucleic Acids Res (25):1078-1079.
Hofmann et al., 1996, "Rapid retroviral delivery of tetracycline inducible genes in a single autoregulatory cassetts", Proc Natl Acad Sci U S A (93):5185-5190.
Holder et al., 2001, "Quantitation of Gene Expression for High-Density Oligonucleotide Arrans: A SAFER Approach", presented in Genelogic Workshop on Law level Analysis of Affymetrix Genechip data, Bethdesa, MD.
Kerr et al., 2000, "Analysis of variance for gene expression microarray data", J Comput Biol (7):819-837.
Kerr et al., 2001, "Statistical design and the analysis of gene expression microarray data", Genet Res Camb (77):123-128.
Koizumi et al., 1988, "Cleavage of specific sites of RNA by designed ribozymes", FEBS Lett (239):285-288.
Koizumi et al., 1988, "Construction of a series of several self-cleaving RNA duplexes using synthetic 21-mers", FEBS Lett (228):228-230.
Lander, 1996, "The new genomics: global views of biology", Science (274):536-539.
Lockhart et al., 1996, "Expression monitoring by hybridization to high-density oligonucleotide arrays", Nat Biotechnol (14):1675-1680.
Lonnstedt et al., 2002, "Replicated Microarray Data", Statistica Sinica (12):31-46.
MacBeath et al., 2000, "Printing proteins as microarrays for high-throughput function determination", Science (289):1760-1763.
Maskos et al., 1992, "Oligonucleotide hybridizations on glass supports: a novel linker for oligonucleotide synthesis and hybridization properties of oligonucleotides synthesised in situ", Nucleic Acids Res (20):1679-1684.
McBride et al., 1983, "An investigation of several deoxynucleoside phosphoramidites useful for synthesizing deoxyoligonucleotides", Tetrahedron Letters (24):245-248.
McGall et al., 1996, "Light-directed synthesis of high-density oligonucleotide arrays using semiconductor photoresists", Proc Natl Acad Sci U S A (93):13555-13560.
Nguyen et al., 1995, "Differential gene expression in the murine thymus assayed by quantitative hybridization of arrayed cDNA clones", Genomics (29):207-216.
No et al., 1996, "Ecdysone-inducible gene expression in mammalian cells and transgenic mice", Proc Natl Acad Sci U S A (93):3346-3351.
Paddison PJ et al., 2002, "Stable suppression of gene expression by RNAi in mammalian cells", Proc Natl Acad Sci U S A (99):1443-1448.
Paulus et al., 1996, "Self-contained tetracycline-regulated retroviral vector system for gene delivery to mammalian cells", J Virol (70):62-67.
Pease et al., 1994, "Light-generated oligonucleotide arrays for rapid DNA sequence analysis", Proc Natl Acad Sci U S A (91):5022-5026.
Petcherski et al., 2000, "LAG-3 is a putative transcriptional activator in the C. elegans Notch pathway", Nature (405):364-368.
Prashar et al., 1996, "Analysis of differential gene expression by display of 3' end restriction fragments of cDNAs", Proc Natl Acad Sci U S A (93):659-663.
Pritchard et al., 2001, "Project normal: defining normal variance in mouse gene expression", Proc Natl Acad Sci U S A (98):13266-13271.
Roberts et al., 2000, "Signaling and circuitry of multiple MAPK pathways revealed by a matrix of global gene expression profiles", Science (287):873-880.
Rocke et al., 2001, "A model for measurement error for gene expression arrays", J Comput Biol (8):557-569.
Sagliocco et al., 1996, "Identification of proteins of the yeast protein map using genetically manipulated strains and peptide-mass fingerprinting", Yeast (12):1519-1533.
Sarver et al., 1990, "Ribozymes as potential anti-HIV-1 therapeutic agents", Science (247):1222-1225.
Schena et al., 1995, "Quantitative monitoring of gene expression patterns with a complementary DNA microarray", Science (270):467-470.
Schena et al., 1996, "Parallel human genome analysis: microarray-based expression monitoring of 1000 genes", Proc Natl Acad Sci U S A (93):10614-10619.
Shalon et al., 1996, "A DNA microarray system for analyzing complex DNA samples using two-color fluorescent probe hybridization", Genome Res (6):639-645.
Shevchenko et al., 1996, "Linking genome and proteome by mass spectrometry: large-scale identification of yeast proteins from two dimensional gels", Proc Natl Acad Sci U S A (93):14440-14445.
Spencer, 1996, "Creating conditional mutations in mammals", Trends Genet (12):181-187.
Tabara et al., 1999, "The rde-1 gene RNA interference and transposon silencing in C. elegans", Cell (99):123-132.
Velculescu et al., 1995, "Serial analysis of gene expression [see comments]", Science (270):484-487.
Wolfinger et al., 2001, "Assessing gene significance from cDNA microarray expression data via mixed models", J Comput Biol (8):625-637.
Wu H et al., 2002, "MAANOVA: A Sotfware Package for the Analysis of Spotted cDNA Microarray Experiments" [online]. [Retrieved Oct. 25, 2002]. Retrieved from the Internet: <URL: http://www.jax.org/churchill/pubs/wu-maannova.pdf>.
Zamore et al., 2000, "RNAi: double-stranded RNA directs the ATP-dependent cleavage of mRNA at 21 to 23 nucleotide intervals", Cell (101):25-33.
Zhu et al., 2001, "Global analysis of protein activities using proteome chips", Science (293):2101-2105.
Ramsey et al. 1992, "Objective Evaluation of Precision Requirements for Geochemical Analysis Using Robust Analysis of Variance," *J. Geochem. Explor.* 44:23-36.

* cited by examiner

ANOVA METHOD FOR DATA ANALYSIS

1. FIELD OF THE INVENTION

The present invention relates to improved Analysis of Variance (ANOVA) methods or analyzing measurement data, e.g., gene/protein expression data.

2. BACKGROUND OF THE INVENTION

DNA array technologies have made it possible to monitor the expression level of a large number of genetic transcripts at any one time (see, e.g., Schena et al., 1995, Science 270:467-470; Lockhart et al., 1996, Nature Biotechnology 14:1675-1680; Blanchard et al., 1996, Nature Biotechnology 14:1649; Ashby et al., U.S. Pat. No. 5,569,588, issued Oct. 29, 1996). Of the two main formats of DNA arrays, spotted cDNA arrays are prepared by depositing PCR products of cDNA fragments with sizes ranging from about 0.6 to 2.4 kb, from full length cDNAs, ESTs, etc., onto a suitable surface (see, e.g., DeRisi et al., 1996, Nature Genetics 14:457-460; Shalon et al., 1996, Genome Res. 6: 639-645; Schena et al., 1996, Proc. Natl. Acad. Sci. U.S.A. 93: 10614-10619; and Duggan et al., Nature Genetics Supplement 21:10-14). Alternatively, high-density oligonucleotide arrays containing thousands of oligonucleotides complementary to defined sequences, at defined locations on a surface are synthesized in situ on the surface by, for example, photolithographic techniques (see, e.g., Fodor et al., 1991, Science 251:767-773; Pease et al., 1994, Proc. Natl. Acad. Sci. U.S.A. 91:5022-5026; Lockhart et al., 1996, Nature Biotechnology 14:1675; McGall et al., 1996, Proc. Natl. Acad. Sci. U.S.A. 93:13555-13560; U.S. Pat. Nos. 5,578,832; 5,556,752; 5,510,270; and 6,040,138). Methods for generating arrays using inkjet technology for in situ oligonucleotide synthesis are also known in the art (see, e.g., Blanchard, International Patent Publication WO 98/41531, published Sep. 24, 1998; Blanchard et al., 1996, Biosensors and Bioelectronics 11:687-690; Blanchard, 1998, in Synthetic DNA Arrays in Genetic Engineering, Vol. 20, J. K. Setlow, Ed., Plenum Press, New York at pages 111-123). Efforts to further increase the information capacity of DNA arrays range from further reducing feature size on DNA arrays so as to further increase the number of probes in a given surface area to sensitivity- and specificity-based probe design and selection aimed at reducing the number of redundant probes needed for the detection of each target nucleic acid thereby increasing the number of target nucleic acids monitored without increasing probe density (see, e.g., Friend et al., International Publication No. WO 01/05935, published Jan. 25, 2001).

By simultaneously monitoring tens of thousands of genes, DNA array technologies have allowed, inter alia, genome-wide analysis of mRNA expression in a cell or a cell type or any biological sample. Aided by sophisticated data management and analysis methodologies, the transcriptional state of a cell or cell type as well as changes of the transcriptional state in response to external perturbations, including but not limited to drug perturbations, can be characterized on the mRNA level (see, e.g., Stoughton et al., International Publication No. WO 00/39336, published Jul. 6, 2000; Friend et al., International Publication No. WO 00/24936, published May 4, 2000). Applications of such technologies include, for example, identification of genes which are up regulated or down regulated in various physiological states, particularly diseased states. Additional exemplary uses for DNA arrays include the analyses of members of signaling pathways, and the identification of targets for various drugs. See, e.g., Friend and Hartwell, International Publication No. WO 98/38329 (published Sep. 3, 1998); Stoughton, International Publication No. WO 99/66067 (published Dec. 23, 1999); Stoughton and Friend, International Publication No. WO 99/58708 (published Nov. 18, 1999); Friend and Stoughton, International Publication No. WO 99/59037 (published Nov. 18, 1999); Friend et al., U.S. Pat. No. 6,218,122.

Protein microarrays are used to monitor the genome-wide protein expression in cells (i.e., the "proteome," Goffeau et al., 1996, Science 274:546-567; Gygi et al., 1999, Nature Biotechnology 17:994-999). Protein microarrays contain binding sites comprise immobilized, preferably monoclonal, antibodies specific to a plurality of protein species encoded by the cell genome (see, e.g., Zhu et al., 2001, Science 293: 2101-2105; MacBeath et al., 2000, Science 289:1760-63; de Wildt et al., 2000, Nature Biotechnology 18:989-994). Protein expression in a cell can also be separated and measured by two-dimensional gel electrophoresis techniques. Two-dimensional gel electrophoresis is well-known in the art and typically involves iso-electric focusing along a first dimension followed by SDS-PAGE electrophoresis along a second dimension. See, e.g., Hames et al., 1990, Gel Electrophoresis of Proteins: A Practical Approach, IRL Press, New York; Shevchenko et al., 1996, Proc. Natl. Acad. Sci. USA 93: 14440-14445; Sagliocco et al., 1996, Yeast 12:1519-1533; Lander, 1996, Science 274:536-539; and Beaumont et al., Life Science News 7, 2001, Amersham Pharmacia Biotech. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

Analysis of Variance (ANOVA) method (see, e.g., Statistics For Experimenters, by Box, Hunter and Hunter, John Wiley & Sons, 1978) are used in gene or protein expression data analysis to determine differential expressions under different treatment conditions. In a one-way ANOVA, there is one experimental factor under investigation. For example, the factor may be the effects of several different compounds vs. the vehicle, which is the baseline reference. For example, when effects of a set of drugs is under investigation, the number of compounds is the number of levels of the factor. The goal is to find out from measured data whether a gene or protein is affected by the compounds. If the expression level of the gene or protein is increased or decreased after the treatments, the gene or protein is said differentially expressed. In a two-way ANOVA, there are two factors under investigation, for example, the drug effect and the dosage effect. Each factor may have multiple levels. Interaction between the two factors is also included in the ANOVA analysis.

ANOVA is often used for determining whether there are statistical differences among the means of measurements in different measurement groups. As an example, the different measurement groups may contain measurements of expression levels of a gene or protein under different drug treatments. In each group, there may be several replicate measurements under the same treatment. First, one finds the within-group variance and the between-group variance. The within-group variance is the measurement variance of measurements within a treatment group. The between-group variance is the measurement variance of the means of different treatment groups. The within-group variance reflects the measurement error of the measurement technology, and the between-group variance includes both the measurement error of the measurement technology and changes caused by different treatments. Then the between-group variance is compared to the within-group variance. If the between-group variance is significantly larger than the within-group variance, it may be concluded that the different treatments have produced statistically significant changes in gene expression levels. In ANOVA analysis, the underlying null-hypothesis is that all treatment groups have the same mean. With the estimated mean squares and degrees of freedom, a p-value of F-statistics can be calculated. The p-value is the probability that the null-hypothesis may be accepted. When the p-value is lower than a given threshold, for example p-value<0.01, the null-hypothesis can be rejected and the alternative hypothesis, which means that some of the expression levels have different means, can be accepted. In other words, some treatments have produced changes in the expression level of the gene.

In a traditional ANOVA method, only measurement quantities, for example, the gene expression intensity or ratio, are used to determine the mean squares and degrees of freedom. The traditional ANOVA relies on a large number of measurement replicates to get a reliable estimation of the within-group variance. However, in gene or protein expression studies, limited by the small quantity of samples and the high cost of carrying out the measurements (such as DNA microarray measurements), the number of replicates is often small. The degrees of freedom is are often small. By random chance, due to the small number of replicates, the estimated within-group variance of expression levels of some of genes or proteins can be very small, often much smaller than the actual measurement error inherent in the measurement technology. As a result, the between-group variance can be much larger than the underestimated within-group variance, leading to a small p-value, which in turn incorrectly indicates a statistically significant difference in the expression levels of the gene or protein. Such incorrect identification of a gene or protein is called a "false positive." High false positive rates are a severe problem in gene expression analysis when the traditional ANOVA method is used. A large number of false positives often requires follow-up validation using other expression profiling technologies. Low degrees-of-freedom also reduce the detection sensitivity. As a result, small changes in differential expression may not be detected. Such missed or detected differentially expressed genes or proteins are called "false negatives."

Measurement errors in microarray experiments are often described by error models (see, e.g., Supplementary material to Roberts et al, 2000, Science, 287:873-880; and Rocke et al., 2001, J. Computational Biology 8:557-569). Measurement errors can also be described as a sum of a common error and a scatter error (see, e.g., Stoughton et al., U.S. Pat. No. 6,351,712). An error-weighted average is used in combining ratio profiles (see, e.g., Stoughton et al., U.S. Pat. No. 6,351, 712).

Various ANOVA models have been described for analyzing microarray data (see, e.g., Kerr et al., 2000, J. Computational Biol. 7:819; Kerr et al., 2001, Genetical Research 77:123; Wolfinger et al., 2001, J. Computational Biol. 8:625; Pritchard et al., 2001, Proc. Natl. Acad. Sci. USA 98:13266; Lonnstedt et al. 2002, Statistica Sinica 12:31; and Wu et al., "MAANOVA: A software package for the Analysis of Spotted cDNA Microarray Experiments," published on the web). These methods are normally applied to transformed microarray data, e.g., logarithmic transformed data, to decompose microarray data into different terms according to sources of variations, e.g., variations due to arrays, dyes, genes, and interactions thereof. Measured expression level changes due to one or more of such sources, e.g., expression level changes as a result of real changes in gene expression in the cells, can then be determined.

It is therefore desirable to have methods that are more accurate in determining differences in measured data among different perturbation groups. It is desirable to have methods for analyzing gene or protein expression with improved false-positive and/or false-negative rate.

Discussion or citation of a reference herein shall not be construed as an admission that such reference is prior art to the present invention.

3. SUMMARY OF THE INVENTION

The present invention provides methods for analyzing measurement data. In the methods of the invention, in addition to the measurement quantities themselves, e.g., measured expression levels of a gene, a second type of inputs, e.g., estimated variances of the measurements, are also used.

In a first aspect of the invention, the invention provides methods of analyzing a plurality of measurements of a variable $\{y_{ti}\}$ in k different measurement groups by ANOVA analysis, where $y_{ti}$ is the ith measurement in the tth measurement group, t=1, 2, ..., k and i=1, 2, ..., $n_t$, $n_t$ being the number of measurements in measurement group t. Each of the k different measurement groups consists of one or more measurements of the variable under a condition common to the measurement group, and each of the measurement $y_{ti}$ has a predetermined measurement variance, e.g., $\sigma_{ti}^2$. In the methods of the invention, k and $n_t$ can be any appropriate integer. In preferred embodiments of the invention, the variable is the transcript level of a gene or the abundance of a protein. Preferably, the transcript level is measured using a DNA microarray. Preferably, the abundance is measured using a protein microarray or two-dimensional gel electrophoresis.

In a preferred embodiment, the invention provides a method for analyzing the plurality of measurements of the variable $\{y_{ti}\}$ comprising (a) determining a within-group variance for the k different measurement groups, wherein the within-group variance consists of a propagated variance and a scattered variance, the propagated variance being determined based on predetermined measurement variances of the plurality of measurements, and the scattered variance being determined based on deviation of each of the plurality of measurements with respect to a mean of measurements in a respective measurement group; (b) determining a between-group variance for the k different measurement groups, wherein the between-group variance is a variance of a plurality of group means, one for each of the k different measurement groups, with respect to a mean of the plurality of measurements, wherein each the group mean is the mean of the one or more measurements in a measurement group; and (c) comparing the within-group variance with the between-group variance, thereby analyzing the plurality of measurements.

In another preferred embodiment, the invention provides a method for analyzing the plurality of measurements of the variable $\{y_{ti}\}$ comprising (a) weighting each measurement $y_{ti}$ with a weighting factor to obtain an error-weighted measurement, wherein the weighting factor is determined based on the predetermined measurement variance of the measurement; (b) determining a within-group variance for the k different measurement groups, wherein the within-group variance consists of a propagated variance and a scattered variance, the propagated variance being determined based on predetermined measurement variances of the plurality of measurements, and the scattered variance being determined based on deviation of each of the plurality of measurements with respect to a mean of error-weighted measurements in a respective measurement group; (c) determining a between-group variance for the k different measurement groups, wherein the between-group variance is a variance of a plurality of group means, one for each of the k different measurement groups, with respect to a mean of the plurality of error-weighted measurements, wherein each group mean is the mean of the one or more measurements in a measurement group; and (d) comparing the within-group variance with the between-group variance, thereby analyzing the plurality of measurements.

In one embodiment of the methods of the invention, the comparing step comprises determining the significance level of a statistical metric by a statistical test, wherein the statistical metric is determined by a method comprising (i) determining a within-group degree of freedom; (ii) determining a between-group degree of freedom; (iii) determining a within-group mean square; (iv) determining a between-group mean square; and (v) calculating the statistical metric.

In still another preferred embodiment, the invention provides an improved ANOVA method for analyzing the plurality of measurements of the variable $\{y_{ti}\}$ in which the improvement comprises determining a within-group variance consisting of a propagated variance and a scattered variance, the propagated variance being determined based on predetermined measurement variances of the one or more measurements, and the scattered variance being determined based on deviation of each of the one or more measurements with respect to a mean of measurements in a respective measurement group.

In the methods of the invention, the within-group variance can be determined based on group variances of the k different measurement groups, each group variance consisting of a measurement group propagated variance and a measurement group scattered variance. Each measurement group propagated variance can be determined based on the predetermined measurement variances of the one or more measurements in the measurement group. The measurement group scattered variance can be a variance of the one or more measurements with respect to the mean of the one or more measurements in the measurement group.

Preferably, the propagated variance for each measurement group is determined according to the equation $$\sigma^2_{\bar{y}_t P} = \frac{\sum_{i=1}^{n_t} \sigma^2_{ti}}{n_t^2}$$

where $\sigma_{\bar{y}_t P}^2$ is the propagated variance. Preferably, the mean of the one or more measurements is determined according to the equation $$\bar{y}_t = \frac{\sum_{i=1}^{n_t} y_{ti}}{n_t}$$

where $\bar{y}_t$ is the mean of the one or more measurements, and the scattered variance is determined according to the equation $$\sigma^2_{\bar{y}_t s} = \frac{1}{(n_t - 1)} \cdot \sum_{i=1}^{n_t} (y_{ti} - \bar{y}_t)^2$$

where $\sigma_{\bar{y}_t s}^2$ is the scattered variance.

In a preferred embodiment, the group propagated variance and the group scattered variance for each group are combined according to the equation $$\sigma_{\bar{y}_t} = \frac{\sigma_{\bar{y}_t P} + (n_t - 1) \cdot \sigma_{\bar{y}_t s}}{n_t}$$

In one embodiment, the method of the invention further comprises a step of determining the predetermined measurement variance for each measurement. In a preferred embodiment, the predetermined measurement variance of each measurement $y_{ti}$ is determined according to an error model, e.g., a three-term error model according to equation $$\sigma_{ti}^2 = c^2 + b^2 \cdot y_{ti} + a^2 \cdot y_{ti}^2$$

wherein $\sigma_{ti}^2$ is the predetermined measurement variance of measurement $y_{ti}$, a is a fractional error coefficient, b is a Poisson error coefficient, and c is a standard deviation of background noise.

In embodiments of the invention which involve error-weighting the measurements or involve using error-weighted measurements, it is preferable that each error-weighted measurement is generated using a weighting factor which is determined based on the predetermined measurement variance of the measurement. In a preferred embodiment, the weighting factor for measurement $y_{ti}$ is determined according to the equation $$w_{ti} = \frac{1}{\sigma_{ti}^2}.$$

In such embodiments, it is preferable that the propagated variance for each measurement group is determined according to the equation $$\sigma^2_{\bar{y}_t P} = \frac{1}{\sum_{i=1}^{n_t} w_{ti}} = \frac{1}{\sum_{i=1}^{n_t} \frac{1}{\sigma_{ti}^2}}$$

where $\sigma_{\bar{y}_t P}^2$ is the propagated variance. In another preferred embodiment, the mean of the one or more error-weighted measurements is determined according to the equation $$\bar{y}_t = \frac{\sum_{i=1}^{n_t} w_{ti} \cdot y_{ti}}{\sum_{i=1}^{n_t} w_{ti}}$$

where $\bar{y}_t$ is the mean of the one or more error-weighted measurements, and wherein the scattered variance is determined according to the equation $$\sigma^2_{\bar{y}_t s} = \frac{1}{(n_t - 1) \cdot \sum_{i=1}^{n_t} w_{ti}} \cdot \sum_{i=1}^{n_t} w_{ti} \cdot (y_{ti} - \bar{y}_t)^2$$

where $\sigma_{\bar{y}_t s}^2$ is the scattered variance.

In such embodiments which involve error-weighting the measurements or involve using error-weighted measurements, it is also preferable that the methods further comprise using an effective number of samples instead of the actual number of samples for each measurement group. In one embodiment, the effective numbers of samples are calculated according to equations $$en_t = \left(\frac{\min(\sigma_{ti})}{\sigma_{\bar{y},p}}\right)^2 = (\min(\sigma_{ti}))^2 \cdot \sum_{i=1}^{n_t} w_{ti}$$

and $$eN = \sum_{t=1}^{k} en_t.$$

In a specific embodiment of the invention, the within-group degree of freedom is calculated according to the equation $$v_R = N - k + \sum_{t=1}^{k} \frac{1}{n_t}$$

where $v_R$ is the within-group degree of freedom the between-group degree of freedom is calculated according to the equation $$v_T = k - 1$$

where $v_T$ is the between-group degree of freedom, the within-group mean square is calculated according to the equation $$s_R^2 = S_R / v_R$$

where $s_R^2$ is the within-group mean square and where $S_R$ is calculated according to the equation $$S_R = \sum_{t=1}^{k} \left[ v_{Rt} \cdot \frac{(\sigma_{\bar{y}_t p} + (n_t - 1) \cdot \sigma_{\bar{y}_t s})^2}{n_t} \right]$$

where $v_{Rt}$ is calculated according to the equation $$v_{Rt} = n_t - 1 + \frac{1}{n_t}$$

and the between-group mean square is calculated according to the equation $$s_T^2 = S_T / v_t$$

where $s_T^2$ is the between-group mean square and where $S_T$ is calculated according to the equation $$S_T = \sum_{t=1}^{k} n_t \cdot (\bar{y}_t - \bar{y})^2$$

where $\bar{y}$ is calculated according to the equation $$\bar{y} = \frac{\sum_{t=1}^{k} \sum_{i=1}^{n_t} y_{ti}}{N}$$

where N is the total number of measurements.

In another specific embodiment of the invention, the within-group degree of freedom is calculated according to the equation $$v_R = eN - k + \sum_{t=1}^{k} \frac{1}{en_t}$$

where $v_R$ is the within-group degree of freedom, $en_t$ is calculated according to the equation $$en_t = \left(\frac{\min(\sigma_{ti})}{\sigma_{\bar{y}_t p}}\right)^2 = (\min(\sigma_{ti}))^2 \cdot \sum_{i=1}^{n_t} w_{ti}$$

and eN is calculated according to the equation $$eN = \sum_{t=1}^{k} en_t,$$

the between-group degree of freedom is calculated according to the equation $$v_T = k - 1$$

where $v_T$ is the between-group degree of freedom, the within-group mean square is calculated according to the equation $$s_R^2 = S_R / v_R$$

where $s_R^2$ is the within-group mean square and where $S_R$ is calculated according to the equation $$S_R = \sum_{t=1}^{k} \left[ V_{Rt} \cdot \frac{(\sigma_{\bar{y}_t p} + (en_t - 1) \cdot \sigma_{\bar{y}_t s})^2}{en_t} \right]$$

where $v_{Rt}$ is calculated according to the equation $$v_{Rt} = n_t - 1 + \frac{1}{n_t}$$

and the between-group mean square is calculated according to the equation $$s_T^2 = S_T / v_T$$

where $s_T^2$ is the between-group mean square and where $S_T$ is calculated according to the equation $$S_T = \sum_{t=1}^{k} en_t \cdot (\bar{y}_t - \bar{y})^2$$

where $\bar{y}$ is calculated according to the equation $$\bar{y} = \frac{\sum_{t=1}^{k}\sum_{i=1}^{n_t} y_{ti}}{N}$$

where N is the total number of measurements.

Preferably, in the methods of the invention, the statistical test is an F-test and the significance level is a p-value determined according to the equation $p\text{value} = 1 - fcdf(s_T^2/s_R^2, v_T, v_R).$ In another aspect of the invention, the invention provides methods of analyzing a plurality of measurements of a variable $\{y_{tij}\}$ in k*n different measurement groups, where $y_{tij}$ is the jth measurement in the tith measurement group, t= 1, 2, ..., n, i=1, 2, ..., k, j=1, ..., $m_{ti}$, $m_{ti}$ being the number of measurements in measurement group ti. Each of the k*n different measurement groups consists of measurements of the variable under common conditions t and i of condition groups N having n different conditions and K having k different conditions, respectively, and each measurement $y_{tij}$ has a predetermined measurement variance, e.g., $\sigma_{tij}^2$. In the methods of the invention, k, n and $m_{ti}$ can be any appropriate integer.

In one preferred embodiment, the invention provides a method comprising (a) determining a within-group variance for the k*n different measurement groups, wherein the within-group variance consists of a propagated variance and a scattered variance, the propagated variance being determined based on predetermined measurement variances of the plurality of measurements, and the scattered variance being determined based on deviation of each of the plurality of measurements with respect to a mean of measurements in a respective measurement group; (b) determining (b1) a between-group variance for condition group K, wherein the between-group variance is a variance of condition group means for the condition group K, one for each condition in the condition group K, with respect to a mean of the plurality of measurements, wherein each condition group mean for the condition group K is the mean of measurements in all measurement groups under a respective condition in the condition group K, or (b2) an interaction variance, wherein the interaction variance is a variance of group interaction means, one for each of the k*n different measurement groups, with respect to a mean of the plurality of measurements and the condition group mean for the condition group K and the condition group mean for the condition group N, wherein each group interaction mean is the mean of measurements in the measurement groups over the number of measurements in the measurement group, and wherein each condition group mean for the condition group K is the mean of measurements in all measurement groups under a respective condition in the condition group K and each condition group mean for the condition group N is the mean of measurements in all measurement groups under a respective condition in the condition group N; and (c) comparing the within-group variance with the between-group variance, thereby analyzing the plurality of measurements. In a preferred embodiment, the method further comprises prior to step (a) a step of weighting each measurement $y_{tij}$ with a weighting factor to obtain an error-weighted measurement, where the weighting factor is determined based on the predetermined measurement variance of the measurement.

In a preferred embodiment, the comparing step comprises determining the significance level of a statistical metric by a statistical test, wherein the statistical metric is determined by a method comprising (i) determining a within-group degree of freedom; (ii) determining a between-group degree of freedom, if the between-group variance is determined in step (b), or an interaction degree of freedom, if the interaction variance is determined in step (b); (iii) determining a within-group mean square; (iv) determining a between-group mean square, if the between-group variance is determined in step (b), or an interaction mean square, if the interaction variance is determined in step (b); and (v) calculating the statistical metric.

In another preferred embodiment, the invention provides an improved two-way ANOVA method for analyzing the plurality of measurements $\{y_{tij}\}$ in which the improvement comprises determining a within-group variance consisting of a propagated variance and a scattered variance, the propagated variance being determined based on predetermined measurement variances of the plurality of measurements, and the scattered variance being determined based on deviation of each of the plurality of measurements with respect to a mean of measurements in a respective measurement group. Preferably, each of the one or more measurements is an error-weighted measurement generated using a weighting factor determined based on the predetermined measurement variance of the measurement.

In embodiments of the invention which involve error-weighting the measurements or involve analyzing error-weighted measurements, it is preferable that each of the one or more measurements is an error-weighted measurement generated using a weighting factor which is determined based on the predetermined measurement variance of the measurement. In a preferred embodiment, the weighting factor for measurement $y_{tij}$ is determined according to the equation $$w_{tij} = \frac{1}{\sigma_{tij}^2}$$

where $\sigma_{tij}^2$ is the predetermined measurement variance of measurement $y_{tij}$.

In the methods of the invention, the within-group variance can be determined based on group variances of the n*k different measurement groups, each group variance consisting of a measurement group propagated variance and a measurement group scattered variance. Each measurement group propagated variance can be determined based on the predetermined measurement variances of the one or more measurements in the measurement group. The measurement group scattered variance can be a variance of the one or more measurements with respect to the mean of the one or more measurements in the measurement group.

Preferably, the propagated variance for each measurement group is determined according to the equation $$\sigma_{\bar{y}_{ti}p}^2 = \frac{\sum_{j=1}^{m_{ti}} \sigma_{tij}^2}{m_{ti}^2}$$

where $\sigma_{\bar{y}_{ti}p}^2$ is the propagated variance. Preferably, the mean of the one or more measurements in a group is determined according to the equation $$\bar{y}_{ti} = \frac{\sum_{j=1}^{m_{ti}} y_{tij}}{m_{ti}}$$

where $\bar{y}_{ti}$ is the mean of the one or more measurements, and the scattered variance is determined according to the equation $$\sigma_{\bar{y}_{ti}s}^2 = \frac{1}{(m_{ti}-1)} \cdot \sum_{j=1}^{m_{ti}} (y_{tij} - \bar{y}_{ti})^2$$

where $\sigma_{\bar{y}_{ti}s}^2$ is the scattered variance.

In a preferred embodiment, the group propagated variance and the group scattered variance for each group are combined according to the equation $$\sigma_{\bar{y}_{ti}} = \frac{\sigma_{\bar{y}_{ti}p} + (m_{ti}-1) \cdot \sigma_{\bar{y}_{ti}s}}{m_{ti}}.$$

In one embodiment, the method of the invention further comprises a step of determining the predetermined measurement variance for each measurement. In a preferred embodiment, the predetermined measurement variance of each measurement $y_{tij}$ is determined according to an error model, e.g., a three-term error model according to equation $$\sigma_{tij}^2 = c^2 + b^2 \cdot y_{tij} + a^2 \cdot y_{tij}^2$$

wherein $\sigma y_{tij}^2$ is the predetermined measurement variance of the measurement $y_{tij}$, a is a fractional error coefficient, b is a Poisson error coefficient, and c is a standard deviation of background noise.

In a specific embodiment of the invention, a between-group variance is determined in step (b). In this embodiment, the within-group degree of freedom is calculated according to the equation $$v_R = N - n \cdot k + \sum_{t=1}^{k} \sum_{i=1}^{n} \frac{1}{m_{ti}}$$

where $v_R$ is the within-group degree of freedom, the between-group degree of freedom is calculated according to the equation $$v_T = k - 1$$

where $v_T$ is the between-group degree of freedom, the within-group mean square is calculated according to the equation $$s_R^2 = S_R/v_R$$

where $s_R^2$ is the within-group mean square and where $S_R$ is calculated according to the equation $$S_R = \sum_{t=1}^{k} \sum_{i=1}^{n} \left[ v_{Rti} \cdot \frac{(\sigma_{\bar{y}_{ti}p} + (m_{ti}-1) \cdot \sigma_{\bar{y}_{ti}s})^2}{m_{ti}} \right]$$

where $v_{Rti}$ is calculated according to the equation $$v_{Rti} = m_{ti} - 1 + \frac{1}{m_{ti}}$$

and the between-group mean square is calculated according to the equation $$s_T^2 = S_T/v_T$$

where $s_T^2$ is the between-group mean square and where $S_T$ is calculated according to the equation $$S_T = \sum_{t=1}^{k} N_t \cdot (\bar{y}_t - \bar{y})^2$$

where $N_t$ is calculated according to the equation $$N_t = \sum_{i=1}^{n} m_{ti}$$

where $\bar{y}$ is calculated according to the equation $$\bar{y} = \frac{1}{N} \sum_{t=1}^{k} \sum_{i=1}^{n} \sum_{j=1}^{m_{ti}} y_{tij}$$

where N is the total number of measurements, and $\bar{y}_t$ is calculated according to the equation $$\bar{y}_t = \frac{\sum_{i=1}^{n} \sum_{j=1}^{m_{ti}} y_{tij}}{N_t}.$$

In such embodiment, the statistical test can be an F-test and the significance level can be a p-value determined according to the equation $$p\text{value} = 1 - fcdf(s_T^2/s_R^2, v_T, v_R).$$

In another specific embodiment of the invention, an interaction variance is determined in step (b). In this embodiment, the within-group degree of freedom is calculated according to the equation $$v_R = N - n \cdot k + \sum_{t=1}^{k} \sum_{i=1}^{n} \frac{1}{m_{ti}}$$

where $v_R$ is the within-group degree of freedom, the interaction degree of freedom is calculated according to the equation $$v_I = (n-1) \cdot (k-1)$$

where $v_I$ is the interaction degree of freedom, the within-group mean square is calculated according to the equation $$s_R^2 = S_R/v_R$$

where $s_R^2$ is the within-group mean square and where $S_R$ is calculated according to the equation $$S_R = \sum_{t=1}^{k} \sum_{i=1}^{n} \left[ v_{Rti} \cdot \frac{(\sigma_{\bar{y}_{ti}p} + (m_{ti}-1) \cdot \sigma_{\bar{y}_{ti}s})^2}{m_{ti}} \right]$$

where $v_{Rti}$ is calculated according to the equation $$v_{Rti} = m_{ti} - 1 + \frac{1}{m_{ti}}$$

and the interaction mean square is calculated according to the equation $$s_I^2 S_I/v_I$$

where $s_I^2$ is the interaction mean square and where $S_I$ is calculated according to the equation $$S_I = \sum_{t=1}^{k} \sum_{i=1}^{n} m_{ti} \cdot (\bar{y}_{ti} - \bar{y}_t - \bar{y}_i + \bar{y})^2$$

where $\bar{y}$ is calculated according to the equation $$\bar{y} = \frac{1}{N} \sum_{t=1}^{k} \sum_{i=1}^{n} \sum_{j=1}^{m_{ti}} y_{tij}$$

where N is the total number of measurements, $\bar{y}_t$ is calculated according to the equation $$\bar{y}_t = \frac{\sum_{i=1}^{n} \sum_{j=1}^{m_{ti}} y_{tij}}{N_t}$$

where $N_t$ is calculated according to the equation $$N_t = \sum_{i=1}^{n} m_{ti}$$

$\bar{y}_i$ is calculated according to the equation $$\bar{y}_i = \frac{\sum_{t=1}^{k} \sum_{j=1}^{m_{ti}} y_{tij}}{N_i}$$

where $N_i$ is calculated according to the equation $$N_i = \sum_{t=1}^{k} m_{ti}$$

and $\bar{y}_{ti}$ is calculated according to the equation $$\bar{y}_{ti} = \frac{\sum_{j=1}^{m_{ti}} y_{tij}}{m_{ti}}.$$

In such embodiment, the statistical test can be an F-test and the significance level can be a p-value determined according to the equation $$p\text{value} = 1 - fcdf(s_I^2/s_R^2, v_I, v_R).$$

In still another aspect of the invention, the invention provides a method of determining if a plurality of measurements in k different measurement groups of a first variable $\{y_{ti}(1)\}$ of a plurality of M different variables are unchanged among the plurality of different measurement groups, wherein a plurality of measurements of each of the plurality of M different variables $\{y_{ti}(j)\}$ in k different measurement groups are available, wherein $y_{ti}(j)$ is the ith measurement of the jth variable in the tth measurement group, $t=1, 2, \ldots, k$; $i=1, 2, \ldots, n_t$, $n_t$ being the number of measurements in measurement group t; and $j=1, 2, \ldots, M$; wherein each measurement group consists of one or more measurements of a respective variable under a condition common to the measurement group, and wherein each measurement $y_{ti}(j)$ has a predetermined measurement variance, the method comprising (a) determining for each of the plurality of M different variables a within-group variance for the k different measurement groups of the variable, wherein the within-group variance consists of a propagated variance and a scattered variance, the propagated variance being determined based on predetermined measurement variances of the plurality of measurements, and the scattered variance being determined based on deviation of each of the plurality of measurements with respect to a mean of measurements in a respective measurement group; (b) determining a between-group variance for the k different measurement groups of the first variable, wherein the between-group variance is a variance of a plurality of group means, one for each of the k different measurement groups, with respect to a mean of the plurality of measurements, wherein each group mean is the mean of the one or more measurements in a measurement group; (c) determining an average within-group variance of measurements of the M different variables, wherein the average within-group variance is an average of within-group variances of the measurements of the plurality of different M variables; and (d) comparing the within-group variance of the first variable with the between-group variance of the first variable and with the average within-group variance, thereby determining if the plurality of measurements of the first variable are unchanged among the plurality of different measurement groups. In the method of the invention, k, $n_t$, and M can be any appropriate integer. The method is equally applicable to any of the other variable among the M variables by repeating steps (a)-(d) such other variables in the plurality of M different variables.

In the method of the invention, the within-group variance for each variable can be determined based on group variances of the k different measurement groups for the variable, each of such group variance consisting of a measurement group propagated variance and a measurement group scattered variance. Each measurement group propagated variance can be determined based on the predetermined measurement variances of the one or more measurements in the measurement group. The measurement group scattered variance can be a variance of the one or more measurements with respect to the mean of the one or more measurements in the measurement group.

Preferably, the propagated variance for each measurement group is determined according to the propagated variance for each measurement group is determined according to the equation $$\sigma_{\bar{y}_t p}^2(j) = \frac{\sum_{i=1}^{n_t} \sigma_{ti}^2(j)}{n_t^2}$$

where $\sigma_{\bar{y}_t,p}^2(j)$ is the propagated variance and $\sigma_{ti}^2(j)$ is the predetermined measurement variance of measurement $y_{ti}(j)$. Preferably, the mean of the one or more measurements is determined according to the equation $$\bar{y}_t(j) = \frac{\sum_{i=1}^{n_t} y_{ti}(j)}{n_t}$$

where $\bar{y}_t(j)$ is the mean of the one or more measurements, and the scattered variance is determined according to the equation $$\sigma_{\bar{y}_t,s}(j)^2 = \frac{1}{(n_t - 1)} \cdot \sum_{i=1}^{n_t} (y_{ti}(j) - \bar{y}_t(j))^2$$

where $\sigma_{\bar{y}_t,s}^2(j)$ is the scattered variance.

In a preferred embodiment, the group propagated variance and the group scattered variance for each group are combined according to the equation $$\sigma_{\bar{y}_t}(j) = \frac{\sigma_{\bar{y}_t,p}(j) + (n_t - 1) \cdot \sigma_{\bar{y}_t,s}(j)}{n_t}.$$

In one embodiment, the method of the invention further comprises a step of determining the predetermined measurement variance for each measurement. In a preferred embodiment, the predetermined measurement variance of each measurement $y_{ti}(j)$ is determined according to an error model, e.g., a three-term error model according to equation $$\sigma_{ti}^2(j) = c^2 + b^2 \cdot y_{ti}(j) + a^2 \cdot y_{ti}(j)^2$$

wherein $\sigma_{ti}^2(j)$ is the predetermined measurement variance of the measurement $y_{ti}(j)$, a is a fractional error coefficient, b is a Poisson error coefficient, and c is a standard deviation of background noise.

Preferably, step of comparing the within-group variance of the first variable with the between-group variance of the first variable is carried out according to the equation $$pvalue = 1 - fcdf(s_T(1)^2/s_R(1)^2, v_T(1), v_R(1))$$

wherein $$v_R(1) = N - k + \sum_{t=1}^{k} \frac{1}{n_t}$$

and $$v_T(1) = k - 1$$

and $$s_R^2(1) = S_R(1)/v_R(1)$$

where $$S_R(1) = \sum_{t=1}^{k} \left[ v_{Rt}(1) \cdot \frac{(\sigma_{\bar{y}_t,p}(1) + (n_t - 1) \cdot \sigma_{\bar{y}_t,s}(1))^2}{n_t} \right]$$

where $$v_{Rt}(1) = n_t - 1 + \frac{1}{n_t}$$

and $$s_T^2(1) = S_T(1)/v_T(1)$$

where $$S_T(1) = \sum_{t=1}^{k} n_t \cdot (\bar{y}_t(1) - \bar{y}(1))^2$$

where $$\bar{y}(1) = \frac{\sum_{t=1}^{k} \sum_{i=1}^{n_t} y_{ti}(1)}{N}$$

where N is the total number of measurements of said first variable; and the comparing the within-group variance of the first variable with the average within-group variance comparing is carried out according to the equation $$SmallError\_pvalue(1) = 1 - fcdf(s_R^2(1)/\bar{s}_R^2, v_R, v_{avg})$$

where $$\bar{s}_R^2 = \frac{1}{M} \cdot \sum_{j=1}^{M} s_R^2(j)$$

wherein $$s_R^2(j) = S_R(j)/v_R(j)$$

where $$S_R(j) = \sum_{t=1}^{k} \left[ v_{Rt}(j) \cdot \frac{(\sigma_{\bar{y}_t,p}(j) + (n_t - 1) \cdot \sigma_{\bar{y}_t,s}(j))^2}{n_t} \right]$$

where $$v_{Rt}(j) = n_t - 1 + \frac{1}{n_t}$$

and where $v_{avg}$ is chosen to be at least about 20 to about 100.

In still another aspect of the invention, the invention provides a method for analyzing variation among a plurality of measurements of a variable $\{y_t\}$, where $y_t$ is the tth measurement, t=1, 2, ..., $n_t$, $n_t$ being the number of measurements. The plurality of measurements are measured under a common condition, and each of the measurements has a predetermined measurement variance. The method comprises (a) determining a propagated variance and a scattered variance, wherein the propagated variance is determined based on predetermined measurement variances of the plurality of measurements, and wherein the scattered variance is a variance of the plurality of measurements with respect to the mean of the plurality of measurements; and (b) comparing the propagated variance and the scattered variance, thereby analyzing variation in the plurality of measurements of the variable. In the method of the invention, n, can be any appropriate integer.

In a preferred embodiment, the propagated variance for each measurement group is determined according to the equation $$\sigma_{\bar{y}_t p}^2 = \frac{\sum_{t=1}^{n_t} \sigma_t^2}{n_t^2}$$

where $\sigma_{\bar{y}_t p}^2$ is the propagated variance and $\sigma_t^2$ is the predetermined measurement variance of measurement $y_t$, and the scattered variance is determined according to the equation $$\sigma_{\bar{y}_t s}^2 = \frac{1}{(n_t - 1)} \cdot \sum_{t=1}^{n_t} (y_t - \bar{y})^2$$

where $\sigma_{\bar{y}_t s}^2$ is the scattered variance and where $$\bar{y} = \frac{\sum_{t=1}^{n_t} y_t}{n_t}.$$

In a preferred embodiment, the method further comprises prior to step (a) a step of weighting each measurement $y_t$ with a weighting factor to obtain an error-weighted measurement, where the weighting factor is determined based on the predetermined measurement variance of the measurement. In one embodiment, the weighting factor is determined according to the equation $$w_t = \frac{1}{\sigma_t^2}.$$

Preferably, the comparing is carried out using an F-test according to the equation Consistency_pvalue=1−$fcdf(\sigma_{\bar{y}_t s}^2/\sigma_{\bar{y}_t p}^2, n_t−1, n_t)$ The invention also provides a computer system comprising a processor and a memory coupled to the processor and encoding one or more programs which programs cause the processor to carry out any one of the methods described above.

The invention also provides a computer program product for use in conjunction with a computer having a processor and a memory connected to the processor, which computer program product comprises a computer readable storage medium having a computer program mechanism encoded thereon. The computer program mechanism may be loaded into the memory of the computer and cause the computer to carry out any one of the methods described above.

4. BRIEF DESCRIPTION OF FIGURES

FIG. 1 is a schematic illustration of an embodiment of the improved ANOVA data processing method. Briefly, the processing blocks in the diagram are listed as following. Pre-Processing (optional)—this pre-processing module handles data normalization and data transformation of, e.g., intensity data. Intensity error of a micro-array measurement has a multiplicative component that is proportional to the intensity itself. To meet the variance homogeneity requirement in ANOVA, the intensity data can be transformed by an error model based transformation which converts the intensity x and intensity error $\sigma_x$ to a new domain y and $\sigma_y$ where the transformed intensity error is constant over the entire range of the transformed intensity. ANOVA—this improved ANOVA module takes two variables y and $\sigma_y$ as inputs. For one-way ANOVA, the module computes one ANOVA p-value for each measurement y. For two-way ANOVA, it computes two p-values of the two factors and one p-value for the interaction between the two factors. The module also estimates the error-weighted mean of replicates in each treatment group and the error of the mean. Post-Processing (optional)—This module inversely transforms the result mean and error from the transformed domain to the original domain.

Figure 2:
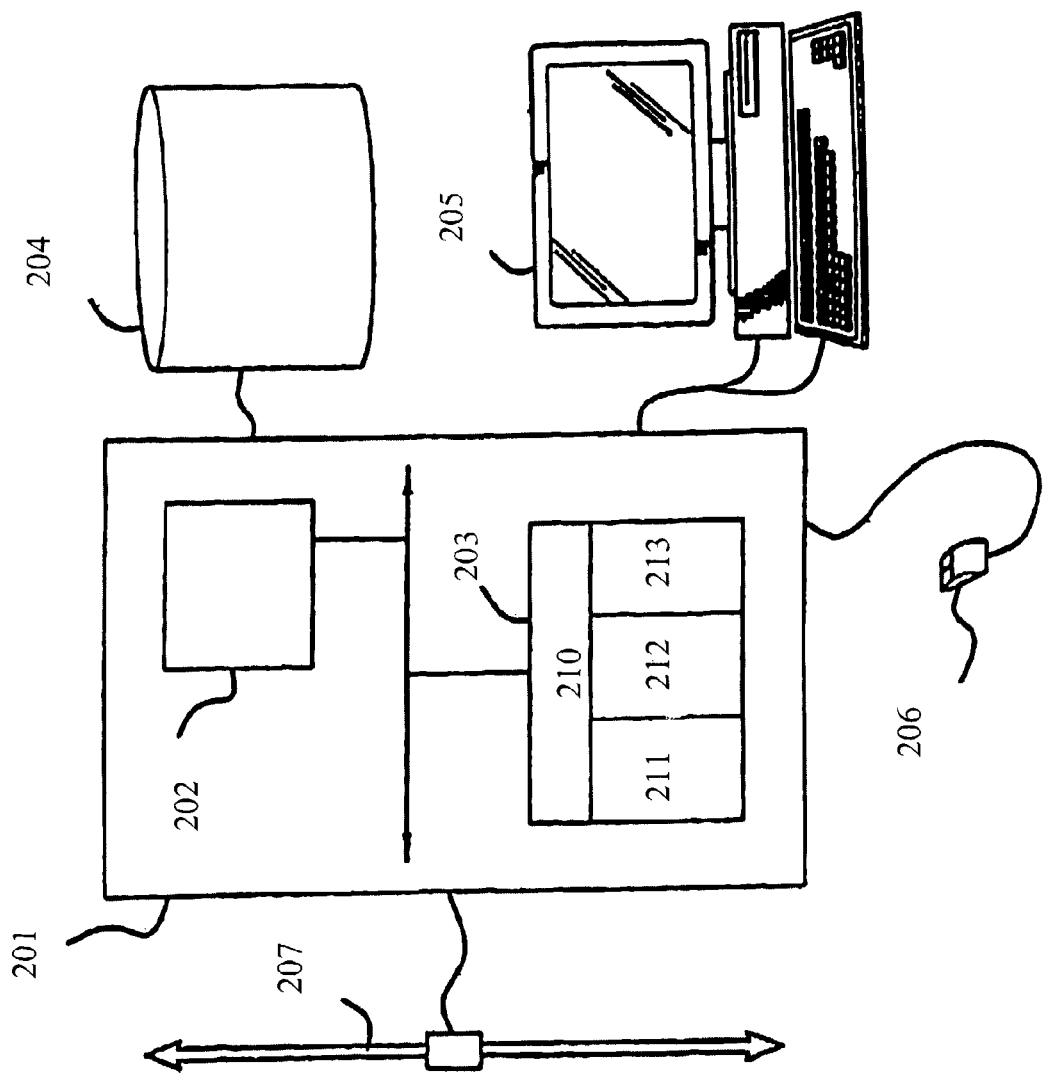

FIG. 2 illustrates an exemplary embodiment of a computer system useful for implementing the methods of this invention.

5. DETAILED DESCRIPTION OF THE INVENTION

The present invention provides improved ANOVA methods for processing and analyzing measured data and transformed data. The methods of the invention is particularly useful for analyzing gene or protein expression data.

In this disclosure, a measurement group refers to a set of one or more replicate measurements of a variable of particular type of sample, e.g., a particular type of cells, a cells sample under a particular condition or perturbation, such as exposure to a drug, a genetic mutation and so on. The variable can be any measurable variable of the sample including but not limited to expression or transcript level of a gene or abundance of a protein, level or concentration of a small cellular molecule, e.g., a metabolite, level of a clinical indicator, e.g., level or concentration of a chemical in blood. As an example, a measurement group may contain a set of gene expression levels of a biological sample which has undergone a particular drug treatment, whereas different measurement groups contain different sets of one or more gene expression levels of the biological sample under different drug treatments, e.g., different doses the same drug, different drugs, different time after the treatment by a drug, etc. In the disclosure, the term "measurement group" is used interchangeably with the terms "treatment group" or "sample group."

In this disclosure, for simplicity reasons, the invention is often described in terms of measured data obtained from a DNA microarray experiment. It will be apparent to a person of ordinary skill in the art that the methods of the present invention are equally applicable to data measured in many other kinds of experiments, e.g., data measured in a protein array experiment or data measured in a two-dimensional (2D) protein gel experiment.

5.1. Biological State and Expression Profile

The state of a cell or other biological sample is represented by cellular constituents (any measurable biological variables) as defined in Section 5.1.1, infra. Those cellular constituents vary in response to perturbations, or under different conditions. The measured data can be measurements of such cellular constituents or measurements of responses of cellular constituents.

5.1.1 Biological State

As used herein, the term "biological sample" is broadly defined to include any cell, tissue, organ or multicellular organism. A biological sample can be derived, for example, from cell or tissue cultures in vitro. Alternatively, a biological sample can be derived from a living organism or from a population of single cell organisms. In preferred embodiments, the biological sample comprises a living cell or organism.

The state of a biological sample can be measured by the content, activities or structures of its cellular constituents. The state of a biological sample, as used herein, is taken from the state of a collection of cellular constituents, which are sufficient to characterize the cell or organism for an intended purpose including, but not limited to characterizing the effects of a drug or other perturbation. The term "cellular constituent" is also broadly defined in this disclosure to encompass any kind of measurable biological variable. The measurements and/or observations made on the state of these constituents can be of their abundances (i.e., amounts or concentrations in a biological sample) e.g., of mRNA or proteins, or their activities, or their states of modification (e.g., phosphorylation), or other measurements relevant to the biology of a biological sample. In various embodiments, this invention includes making such measurements and/or observations on different collections of cellular constituents. These different collections of cellular constituents are also called herein aspects of the biological state of a biological sample.

One aspect of the biological state of a biological sample (e.g., a cell or cell culture) usefully measured in the present invention is its transcriptional state. In fact, the transcriptional state is the currently preferred aspect of the biological state measured in this invention. The transcriptional state of a biological sample includes the identities and abundances of the constituent RNA species, especially mRNAs, in the cell under a given set of conditions. Preferably, a substantial fraction of all constituent RNA species in the biological sample are measured, but at least a sufficient fraction is measured to characterize the action of a drug or other perturbation of interest. The transcriptional state of a biological sample can be conveniently determined by, e.g., measuring cDNA abundances by any of several existing gene expression technologies. One particularly preferred embodiment of the invention employs DNA arrays for measuring mRNA or transcript level of a large number of genes. The other preferred embodiment of the invention employs DNA arrays for measuring expression levels of a large number of genes or exons in the genome of an organism.

Another aspect of the biological state of a biological sample usefully measured in the present invention is its translational state. The translational state of a biological sample includes the identities and abundances of the constituent protein species in the biological sample under a given set of conditions. Preferably, a substantial fraction of all constituent protein species in the biological sample is measured, but at least a sufficient fraction is measured to characterize the action of a drug of interest. As is known to those of skill in the art, the transcriptional state is often representative of the translational state.

Still another aspect of the biological state of a biological sample is its small molecule state, e.g., metabolic state. The small molecule state of a biological sample comprises identities and abundances of small molecules present in a cell. Small molecules refer to molecules of molecular weights of less than about 5000, including but are not limited to sugars, fatty acids, amino acids, nucleotides, intermediates of cellular processes, e.g., intermediates of metabolic and signaling pathways.

Other aspects of the biological state of a biological sample are also of use in this invention. For example, the activity state of a biological sample, as that term is used herein, includes the activities of the constituent protein species (and also optionally catalytically active nucleic acid species) in the biological sample under a given set of conditions. As is known to those of skill in the art, the translational state is often representative of the activity state.

This invention is also adaptable, where relevant, to "mixed" aspects of the biological state of a biological sample in which measurements of different aspects of the biological state of a biological sample are combined. For example, in one mixed aspect, the abundances of certain RNA species and of certain protein species, are combined with measurements of the activities of certain other protein species. Further, it will be appreciated from the following that this invention is also adaptable to other aspects of the biological state of the biological sample that are measurable.

The biological state of a biological sample (e.g., a cell or cell culture) is represented by a profile of some number of cellular constituents. Such a profile of cellular constituents can be represented by the vector S, $$S = [S_1, \ldots S_i, \ldots S_k] \qquad (1)$$

where $S_i$ is the level of the i'th cellular constituent, for example, the transcript level of gene i, or alternatively, the abundance or activity level of protein i. In preferred embodiments, k is more than 2, preferably more than 10, more preferably more than 100, still more preferably more than 1000, still more preferably more than 10,000, still more preferably more than 25,000, still more preferably more than 50,000, and most preferably more than 100,000.

In some embodiments, cellular constituents are measured as continuous variables. For example, transcriptional rates are typically measured as number of molecules synthesized per unit of time. Transcriptional rate may also be measured as percentage of a control rate. However, in some other embodiments, cellular constituents may be measured as categorical variables. For example, transcriptional rates may be measured as either "on" or "off", where the value "on" indicates a transcriptional rate above a predetermined threshold and value "off" indicates a transcriptional rate below that threshold.

5.1.2 Biological Responses and Expression Profiles

The responses of a biological sample to a perturbation, i.e., under a condition, such as the application of a drug, can be measured by observing the changes in the biological state of the biological sample. For example, the responses of a biological sample can be responses of a living cell or organism to a perturbation, e.g., application of a drug, a genetic mutation, an environmental change, and so on, to the living cell or organism. A response profile is a collection of changes of cellular constituents. In the present invention, the response profile of a biological sample (e.g., a cell or cell culture) to the perturbation m is defined as the vector $v^{(m)}$:

$$v^{(m)} = [v_1^{(m)}, \ldots v_i^{(m)}, \ldots v_k^{(m)}] \qquad (2)$$

Where $v_i^m$ is the amplitude of response of cellular constituent i under the perturbation m. In some particularly preferred embodiments of this invention, the biological response to the application of a drug, a drug candidate or any other perturbation, is measured by the induced change in the transcript level of at least 2 genes and/or proteins, preferably more than 10 genes and/or proteins, more preferably more than 100 genes and/or proteins, still more preferably more than 1000 genes and/or proteins, still more preferably more than 10,000 genes and/or proteins, still more preferably more than 25,000 genes and/or proteins, still more preferably more than 50,000 genes and/or proteins, and most preferably more than 100,000 genes and/or proteins. In another preferred embodiment of the invention, the biological response to the application of a drug, a drug candidate or any other perturbation, is measured by the induced change in the expression levels of a plurality of exons in at least 2 genes and/or proteins, preferably more than 10 genes and/or proteins, more preferably more than 100 genes and/or proteins, still more preferably more than 1000 genes and/or proteins, still more preferably more than 10,000 genes and/or proteins, still more preferably more than 25,000 genes and/or proteins, still more preferably more than 50,000 genes and/or proteins, and most preferably more than 100,000 genes and/or proteins.

In some embodiments of the invention, the response is simply the difference between biological variables before and after perturbation. In some preferred embodiments, the response is defined as the ratio of cellular constituents before and after a perturbation is applied. In other embodiments, the response may be a function of time after the perturbation, i.e., $v^{(m)} = v^{(m)}(t)$. For example $v^{(m)}(t)$ may be the difference or ratio of cellular constituents before the perturbation and at time t after the perturbation.

In some preferred embodiments, $v_i^m$ is set to zero if the response of gene i is below some threshold amplitude or confidence level determined from knowledge of the measurement error behavior. In such embodiments, those cellular constituents whose measured responses are lower than the threshold are given the response value of zero, whereas those cellular constituents whose measured responses are greater than the threshold retain their measured response values. This truncation of the response vector is a good strategy when most of the smaller responses are expected to be greatly dominated by measurement error. After the truncation, the response vector $v^{(m)}$ also approximates a 'matched detector' (see, e.g., Van Trees, 1968, *Detection, Estimation, and Modulation Theory Vol. I*, Wiley & Sons) for the existence of similar perturbations. It is apparent to those skilled in the art that the truncation levels can be set based upon the purpose of detection and the measurement errors. For example, in some embodiments, genes whose transcript level changes are lower than two fold or more preferably four fold are given the value of zero.

In some preferred embodiments, perturbations are applied at several levels of strength. For example, different amounts of a drug may be applied to a biological sample to observe its response. In such embodiments, the perturbation responses may be interpolated by approximating each by a single parameterized "model" function of the perturbation strength u. An exemplary model function appropriate for approximating transcriptional state data is the Hill function, which has adjustable parameters a, $u_0$, and n.

$$H(u) = \frac{a(u/u_0)^n}{1+(u/u_0)^n} \quad (3)$$

The adjustable parameters are selected independently for each cellular constituent of the perturbation response. Preferably, the adjustable parameters are selected for each cellular constituent so that the sum of the squares of the differences between the model function (e.g., the Hill function, Equation 3) and the corresponding experimental data at each perturbation strength is minimized. This preferable parameter adjustment method is well known in the art as a least squares fit. Other possible model functions are based on polynomial fitting, for example by various known classes of polynomials. More detailed description of model fitting and biological response has been disclosed in Friend and Stoughton, Methods of Determining Protein Activity Levels Using Gene Expression Profiles, PCT publication WO 99/59037, which is incorporated herein by reference in its entirety for all purposes.

5.2. Data Transformations

Measured data obtained in a microarray experiment often contain errors due both to the inherent stochastic nature of gene expression and to measurement errors from various external sources. The many sources of measurement error that may occur in a measured signal include those that fall into three categories—additive error, multiplicative error, and Poisson error. The signal magnitude-independent or intensity-independent additive error includes errors resulted from, e.g., background fluctuation, or spot-to-spot variations in signal intensity among negative control spots, etc. The signal magnitude-dependent or intensity-dependent multiplicative error, which is assumed to be directly proportional to the signal intensity, includes errors resulted from, e.g., the scatter observed for ratios that should be unity. The multiplicative error is also termed fractional error. The third type of error is a result of variation in number of available binding sites in a spot. This type of error depends on the square-root of the signal magnitude, e.g., measured intensity. It is also called the Poisson error, because it is believed that the number of binding sites on a microarray spot follows a Poisson distribution, and has a variance which is proportional to the average number of binding sites.

5.2.1. Error Model Based Transformations

In a preferred embodiment, measured data are first transformed by an error model based transformation before analyzed by the improved ANOVA method of the invention. The results from the ANOVA analysis can be transformed back by an appropriate inverse transformation. An error model based data transformation method is described in Weng, U.S. Provisional Patent Application No. 60/353,845, filed on Jan. 31, 2002, which is incorporated by reference herewith in its entirety.

5.2.1.1. Error Models

Errors in measured data can be described by error models (see, e.g., Supplementary material to Roberts et al, 2000, Science, 287:873-880; and Rocke et al., 2001, J. Computational Biology 8:557-569). In preferred embodiments, an error model (see, e.g., Supplementary material to Roberts et al, 2000, Science, 287:873-880; and Rocke et al., 2001, J. Computational Biology 8:557-569) contains two or three error terms to describe the dominant error sources. In a two-term error model, a first error term is used to describe the low-level additive error which comes from, e.g., the background of the array chip. Since this additive error has a constant variance, in this disclosure, it is also called the constant error. The constant error is independent from the hybridization levels of individual spots on a microarray. It may come from scanner electronics noise and/or fluorescence due to nonspecific binding of fluorescence molecules to the surface of the microarray. In one embodiment, this constant additive error is taken to have a normal distribution with a mean bkg and a standard deviation $\sigma_{bkg}$. After background level subtraction, which is typically applied in microarray data processing, the additive mean bkg becomes zero. In this disclosure, it is often assumed that the background intensity offset has been corrected. An ordinary skilled artisan in the art will appreciate that in cases where the background mean is not corrected, the methods of the invention can be used with an additional step of making such a correction.

The second error source is the multiplicative error that is the combined result of the speckle noise inherent in the coherent laser scanner and the fluorescence dye related noise. The multiplicative error is also called fractional error because its level is directly proportional to the magnitude of the measured signal, e.g., the measured intensity level. It is the dominant error source at high intensity levels. In one embodiment in which the measured signal is obtained from a microarray experiment, the standard deviation of the fractional error in the k'th spot can be approximated as $$\sigma_{frac}(k) \approx a \cdot x(k) \quad (4)$$

where x(k) is the measured intensity in the k'th spot. The constant a in Equation 4 is termed fractional error coefficient, and describes the proportion of the fractional error to the intensity of the measured signal. In one embodiment, the constant has a value in the range of 0.1 to 0.2. This constant may vary depending on the particular microarray technology used for obtaining the measured signal and/or the particular hybridization protocol used in the measurement. In one embodiment, parameter a is determined during the error building phase by measuring the variance of the log ratio near the high intensity side in a same-vs.-same ratio experiment where the intensities in the ratio numerator and denominator come from the same sample and treatment. At high intensities, the variance of log ratio $x_1$ over $x_2$ relates to parameter a:

$$\mathrm{Var}\{\ln(x_1/x_2)\} \approx \frac{(a \cdot x_1)^2}{x_1^2} + \frac{(a \cdot x_2)^2}{x_2^2} = 2 \cdot a^2 \quad (5)$$

when $x_1$ and $x_2 \gg \sigma_{bkg}$. In one embodiment, $x_1$ and $x_2$ are at least 4, 10, 50, 100, or 200 times $\sigma_{bkg}$.

In a two-term error model, the measurement error in a measured signal, e.g., measured intensity, x(k) can be defined as $$\sigma_x(k) = \sqrt{\sigma_{bkg}(k)^2 + \sigma_{frac}(k)^2} \approx \sqrt{\sigma_{bkg}(k)^2 + a^2 \cdot x(k)^2} \quad (6)$$

In a preferred embodiment of the invention, the background noise variances in Equation 6 are taken as slightly different in different microarray spots or regions of a microarray chip. In one embodiment, the difference is less than 20%, 10%, 5%, or 1%.

In a three-term error model, an extra square-root term is included to describe measurement errors originated from variation in the number of available binding sites in a microarray spot. This term is also called the Poisson term. In one embodiment, without knowledge of actual number of binding sites in a microarray spot, the measured intensity is used to provide an estimate of the average number of binding sites. In such an embodiment, the Poisson error can be approximated as $$\sigma_{Poisson}(k) \approx b \cdot \sqrt{x(k)} \quad (7)$$

where parameter b is an overall proportional factor, termed Poisson error coefficient. In a three-term error model, the measurement error in a measured signal, e.g, a measured fluorescence intensity, x(k) can be defined as $$\sigma_x(k) = \sqrt{\sigma_{bkg}(k)^2 + \sigma_{Poisson}(k)^2 + \sigma_{frac}(k)^2} \quad (8)$$
$$\approx \sqrt{\sigma_{bkg}(k)^2 + b^2 \cdot x(k) + a^2 \cdot x(k)^2}$$

In a preferred embodiment, during error model development, when $\sigma_{bkg}$ and parameter a have been determined, parameter b in Equation 8 is determined by measuring the intensity variance in the middle intensity ranges of the same-vs.-same experiments. In one embodiment, the intensity variance is measured in the 25 to 75 percentile range, 35 to 65 percentile range, or 45 to 50 percentile range for determination of b.

In a preferred embodiment, after the error model development phase, parameters a and b are fixed for an error model under a given microarray technology and experiment protocol. The background noise $\sigma_{bkg}$ can be estimated for each particular microarray experiment. In another preferred embodiment, when a set of replicate experiments are carried out, the background noise $\sigma_{bkg}$ for the set can be obtained by averaging the background noise estimated for each of the replicate experiments.

The two-term error model as described by Equation 6 can been seen as a simplified version of the three-term error model described by Equation 8 by setting the Poisson parameter b to zero. In this disclosure, Equation 8 is used as the general mathematical description of error models. It will be apparent to an ordinarily skilled artisan that any results obtained based on Equation 8 are also applicable to a two-term error model by setting the Poisson parameter b to zero.

It will be apparent to an ordinarily skilled artisan that other methods may also be used to determine an error model (see, e.g., Rocke et al., 2001, J. Computational Biology 8:557-569).

5.2.1.2. Intensity Transformations

It is clear from Equation 8 that microarray intensity measurements do not meet the constant-variance requirement. There are different measurement errors (or variances) in different intensities. The intensity error is a function of intensity itself. To overcome this problem, a function $f(\ )$ is needed to transform measured data, e.g. the intensity data, x to a new domain y in which the variance becomes a constant. All analysis and data processing can then be carried out in the transformed domain. In a preferred embodiment, such a transformation is described as $$y(k) = f(x(k)), \text{ for all } x \text{ and} \quad (9)$$

$$\sigma_y(k) \approx C, \text{ for all } x \text{ where } C \text{ is a constant.} \quad (10)$$

Preferably the transformation works for both positive and negative (e.g, negative signals obtained after background subtraction) x. More preferably the transformation meets the following additional constraints:
 (i) Monotonic: If $x(k_1) > x(k_2)$, then $y(k_1) > y(k_2)$ for all x;
 (ii) Zero intercept: $f(0)=0$; and
 (iii) Smooth: The first and the second derivatives of the function f should be continuous functions.

Still more preferably, an inverse transformation function g exists so that the transformed data in the transformed domain can be transformed back to the original domain. The inverse transformation does the following operation:

$$x(k) = g(y(k)), \text{ for all } y \quad (11)$$

Preferably, the inverse transformation function g meets above four constraints as well. In one embodiment, the error in the inversely transformed intensity can be determined when the first derivative $f'(\ )$ of the forward transformation function $f$ is available:

$$\sigma_x(k) \approx \frac{\sigma_y(k)}{df(x(k))/dx(k)} = \frac{\sigma_y(k)}{f'(x(k))} \qquad (12)$$

It is most preferable that the forward transformation function $f$, its first derivative $f'$, and the inverse transformation function g are all in analytical closed-forms.

A transformation based on an error model is provided and used to transform measured data obtained in an experiment to a transformed domain such that the measurement errors in transformed data are equal to the measurement errors in the measured data normalized by errors determined based on an error model. As used in this disclosure, such an measurement error, i.e., a measurement error which equals the measurement error in the measured signal normalized by an error determined based on an error model, is also referred to as a normalized error. Any suitable error model can be used in the invention. In a preferred embodiment, the error model is a two-term or a three-term error model described in Section 5.1.1.1. In a particularly preferred embodiment, the variance of the transformed data in the transformed domain is close to a constant. More preferably, the transformation meets all requirements discussed in Section 5.2.1.2. The basic concept of the new transformation method is to apply an error model to normalize errors in real measurements, e.g., standard deviations in measured data, such that the normalized errors are close to a constant. Then a transformation function $f(\ )$ is found by the integration of the normalization function. The methods are applicable to any set of measured data whose errors can be described by a particular error model.

In a specific embodiment, the real measurement standard deviation $\Delta x$ is for the positive intensity $x>0$. The real standard deviation $\Delta x$ is usually known before the transformation. An error model in Equation 8 provides $\sigma_x$ that is an estimate of the real standard deviation $\Delta x$ for different intensities. In one embodiment, $\Delta x$ is an error determined by the experiment. In another embodiment, $\Delta x$ is calculated using an error model of the experiment. In a preferred embodiment, $\Delta x$ is chosen to be the larger of an experimentally determined error or an error model-calculated error. Assuming the transformed standard deviation is $\Delta y$, the following approximation relates the two errors with the first derivative function of the transformation:

$$f'(x) = \frac{dy}{dx} \approx \frac{\Delta y}{\Delta x} \qquad (13)$$

If the equation is rearranged, one obtains $$\Delta y \approx \Delta x \cdot f'(x) \qquad (14)$$

Because Equation 8 is an approximation of $\Delta x$, if a normalization function $y'$ is defined as follows:

$$y' = f'(x) = \frac{1}{\sqrt{c^2 + b^2 \cdot x + a^2 \cdot x^2}}, \text{ for } x > 0, \qquad (15)$$

where a, b, and c are defined as in Section 5.2.1.1, one can expect that the variance of y is close to a constant.

Equation 15 provides an analytical form of the first derivative function of the desired transformation. To obtain the transformation function itself, both sides of Equation 15 are integrated:

$$y = f(x) = \int f'(x) \cdot dx = \int \frac{dx}{\sqrt{c^2 + b^2 \cdot x + a^2 \cdot x^2}}, \text{ for } x > 0 \qquad (16)$$

Fortunately, the integral in Equation 16 does have an analytical solution. By using a symbolic-solution software, such as Mathematica, or using an integral table, the solution is obtained as $$y = f(x) = \frac{\ln\left(\frac{b^2 + 2 \cdot a^2 \cdot x}{a} + 2 \cdot \sqrt{c^2 + b^2 \cdot x + a^2 \cdot x^2}\right)}{a} + d, \qquad (17)$$
for $x > 0$ Applying the zero intercept constraint (ii) in Section 5.2.1.2, i.e., y=0 when x=0, the constant d in Equation 17 is found to be $$d = \frac{-\ln\left(\frac{b^2}{a} + 2 \cdot c\right)}{a} \qquad (18)$$

As indicated in Equation 11 in Section 5.2.1.2, preferably one finds the inverse transformation function g(y) so that the transformed intensity y can be converted back to the original x scale whenever necessary. By using linear algebra or a symbolic-solution software, such as Maple, one finds $$x = g(y) = \frac{-(4 \cdot a^2 \cdot c^2 - a^2 \cdot e^{2a(y-d)} + 2 \cdot a \cdot b^2 \cdot e^{a(y-d)} - b^4)}{4 \cdot a^3 \cdot e^{a(y-d)}}, \qquad (19)$$
for $y > 0$ To complete the forward and the inverse transformation pair for both intensity and its error, the standard deviation of the inversely transformed intensity can be estimated by using Equation 12.

In a specific embodiment, the transformation function can be further defined to be symmetric to zero for all x. When x<0, the absolute value |x| is used to replace x in the forward transformation in Equation 17 and to give a negative sign to the result y. In the inverse transformation in Equation 19, when y<0, the absolute value |y| is used to replace y and to give a negative sign to the result x.

Under the forward transformation, the estimated transformed error $\sigma_y$ is one over all intensity ranges of x or y, so that constant C=1 in Equation 10. The transformation also meets all other requirements and constraints stated in Section 5.2.1.2. In addition, the transformation has several other interesting properties:

$$y = f(x) \approx \frac{\ln(4 \cdot a \cdot x)}{a}, \text{ when } x \text{ is very large} \qquad (20)$$

$$y' = f'(x) \approx \frac{1}{c}, \text{ when } |x| \text{ is very small} \qquad (21)$$

The transformation described in this section is applicable to any measured data in which the errors can be described by a three-term error model. In preferred embodiments, the measured data are measured in a microarray gene expression experiment. In other preferred embodiments, the measured data are measured in a protein array experiment or a 2D gel protein experiment.

In one preferred embodiment, the measured data are signal data obtained in an microarray experiment in which two spots or probes on a microarray are used for obtaining each measured signal, one comprising the targeted nucleotide sequence, i.e., the target probe (TP), e.g., a perfect-match probe, and the other comprising a reference sequence, i.e., a reference probe (RP), e.g., a mutated mismatch probe. The RP probe is used as a negative control, e.g., to remove undesired effects from non-specific hybridization. In one embodiment, the measured signal obtained in such a manner is defined as the difference between the intensities of the TP and RP, $x_{TP} - x_{RP}$. In such an embodiment, the fractional error, the Poisson error, and the background constant error $\sigma_{bkg}$ are described respectively according to equations $$\sigma_{frac}(k) \approx a \cdot x(k) = a \cdot \sqrt{x_{TP}(k)^2 + x_{RP}(k)^2} \qquad (22)$$

$$\sigma_{Poisson}(k) \approx b \cdot \sqrt{x(k)} b \cdot (x_{TP}(k)^2 + x_{RP}(k)^2)^{1/4} \qquad (23)$$

$$\sigma_{bkg}(k) = \sqrt{\sigma_{bkg\_TP}(k)^2 + \sigma_{bkg\_RP}(k)^2} \qquad (24)$$

The transformation described in this section remains applicable if Equations 22-24 are used to calculate the fractional error, the Poisson error and the background constant error, respectively. In one embodiment, the TP probe is a perfect-match probe (PM), and the RP probe is a mismatch probe (MM) (see, e.g., Lockhart et al., 1996, *Nature Biotechnology* 14:1675). In another embodiment, the RP probe is a reverse probe of the TP probe, i.e., the RP probe has a sequence that is the reverse complement of the TP probe (see, Shoemaker et al., U.S. patent application Ser. No. 09/781,814, filed on Feb. 12, 2001; and Shoemaker et al., U.S. patent application Ser. No. 09/724,538, filed on Nov. 28, 2000).

It will be apparent to one skilled in the art that although the transformations as described by equations 17 and 19 are preferably carried out using parameters a, b, and c chosen based on a three-term error model, the transformations as described by equations 17 and 19 can also be used by replacing parameters a, b, and c with other parameters. Embodiments using such parameters are also encompassed by the present invention.

5.2.2. Other Transformations

Another transformation that can be used to transform the data before ANOVA analysis is a logarithm transformation:

$$y(k) = f(x(k)) = \ln(x(k)), \text{ for } x > 0 \qquad (25)$$

In Equation 8, when intensity x is very high, the fractional error is the dominant error source. In this case, the standard deviation of y is approximately a constant:

$$\sigma_y(k) \approx \sigma_x(k) \cdot f'(x(k)) \approx \frac{a \cdot x(k)}{x(k)} = a, \text{ when } x \text{ is very large} \qquad (26)$$

When intensity x is low, the standard deviation of y is inversely proportional to x, and is approaching infinity:

$$\sigma_y(k) \approx \sigma_x(k) \cdot f'(x(k)) \approx \frac{\sigma_{bkg}(k)}{x(k)}, \text{ when } x \text{ is very small} \qquad (27)$$

Still another transformation that can be used to transform the data is a piecewise hybrid transformation (see, e.g., D. Holder, et al, "Quantitation of Gene Expression for High-Density Oligonucleotide Arrays: A SAFER Approach", presented in Genelogic Workshop on Low Level Analysis of Affymetrix Genechip® data, Nov. 19, 2001, Bethesda, Md. This hybrid transformation uses a linear function at the low intensity side and a logarithm function for high intensities. An arbitrary parameter c' defines the boundary between the linear and the logarithmic functions. Equation 28 is the mathematical definition of the hybrid transformation function.

$$y(k) = f(x(k)) = x(k), \text{ for } 0 \leq x(k) < c'$$
$$y(k) = f(x(k)) = c' \cdot \ln(x(k)/c') + c', \text{ for } x(k) \geq c' \qquad (28)$$
$$y(k) = f(x(k)) = 0, \text{ for } x(k) < 0$$

In one embodiment, parameter c' in Equation 28 is chosen to be 20. Errors of the hybrid-transformed intensities can be estimated as $$\sigma_y(k) \approx \sigma_x(k) \cdot f'(x(k)) = \sigma_x(k), \text{ for } 0 \leq x(k) < c'$$
$$\sigma_y(k) \approx \sigma_x(k) \cdot f'(x(k)) = c' \cdot \sigma_x(k)/x(k), \text{ for } x(k) \geq c' \qquad (29)$$

5.3. Improved ANOVA Methods for Analyzing Measured Data

The present invention provides improved ANOVA methods for processing and analyzing measured data and transformed data, e.g., data transformed by a method described in Section 5.2. When transformed data are analyzed by the improved ANOVA method of the invention, it is optional to transform the results back by an appropriate inverse transformation.

5.3.1. ANOVA Methods

Analysis of Variance (ANOVA) is a widely used method for analyzing gene or protein expression data (see, e.g., Statistics For Experimenters, Box, Hunter and Hunter, John Wiley and Sons, 1978; Siegel et al., Nonparametric statistics for the behavioural sciences, McGraw Hill, $2^{nd}$ edition, 1998; Conover, Practical Nonparametric Statistics, John Wiley and Sons, $3^{rd}$ edition, 1998; Altman, Practical Statistics for Medical Research, CRC Press, 1991; Berry, Statistical Methods in Medical Research, Blackwell Science, Inc., 2001). ANOVA is a method for determining whether there are statistical differences among the means of different measurement groups. Each different measurement group contains one or more replicate measurements of a particular type of sample, e.g., a particular type of cells, a cells sample under a particular condition or perturbation, such as exposure to a drug, a genetic mutation and so on. For example, gene expression levels or protein abundances or activity levels from cells under different conditions or perturbations, including but are not limited to different drug treatments, e.g., different doses the a particular drug, different drugs, different time after the treatment by a drug, etc., can be measured using DNA or protein micro-arrays and 2D gel electrophoresis or mass spectrometry. In such cases, each measurement group contains replicate measurements of expression level of a gene or abundance/activity level of a protein in cells under a condition or perturbation common to the measurements, whereas different measurement groups contain measurements of expression level of the gene or abundance/activity levels of the protein in cells under conditions or perturbations different among different groups. In ANOVA, one first finds the within-group variance, i.e., variance of individual measurements, and the between-group variance, i.e., variance of the means of different treatment groups. The within-group variance reflects the measurement error of the measurement technology, while the between-group variance includes both the measurement error of the measurement technology and the changes caused by different treatments. The between-group variance is then compared to the within-group variance. If the between-group variance is significantly larger than the within-group variance, it may be concluded that the different treatments have produced statistically significant changes in measurements, e.g., gene expression levels. In this disclosure, the term "treatment group" or "sample group" are also used. These terms and the term "measurement group" are intended to be equivalent and are used interchangeably. In the disclosure, the term "average" and "mean" are also used interchangeably.

In ANOVA, the underlying null-hypothesis H, is that all treatment groups have the same mean, i.e., the mean of each treatment group does not change among different treatment groups. For example, in cases of expression levels of a gene or abundances of a protein under different conditions, H, is that the mean expression level of the gene or abundances of the protein is the same under the different conditions. To test H, a statistical distribution of residues can be selected. For example, in ANOVA F-statistics is often used ith an underlying assumption of normal distribution. A statistical metric can then be chosen. The significance level of the statistical metric is then determined. If the significance level is greater than a given threshold, the null-hypothesis is accepted, whereas if the significance level is lower than the threshold the null-hypothesis is rejected and the alternative hypothesis H, that one or more measurement groups have different means is accepted. Alternatively, a randomization method, e.g., permutation, can be employed to obtain a distribution free significance level (see, e.g., Wu et al., "MAANOVA: A software package for the Analysis of Spotted cDNA Microarray Experiments," published on the web, which is incorporated by reference herein in its entirety). A skilled person in the art will be able to select an appropriate statistical test once the data to be analyzed are given.

To calculate a statistical metric, e.g., a metric for F-statistics, assuming there are a total of k different treatment groups, e.g., k different compounds or k different dose levels of one compound, and a total of $n_t$ replicate measurements in treatment group t, then the ith replicate measurement in the tth treatment group is written as $y_{ti}$, where the treatment index t is from 1 to k, and the replicate index i is from 1 to $n_t$. The total number of measurements is $$N = \sum_{t=1}^{k} n_t \qquad (30)$$

The grand average of all N measurements is $$\bar{y} = \frac{1}{N} \sum_{t=1}^{k} \sum_{i=1}^{n_t} y_{ti} \qquad (31)$$

For a given treatment group t, the group average is $$\bar{y}_t = \frac{1}{n_t} \sum_{i=1}^{n_t} y_{ti} \qquad (32)$$

The traditional one-way ANOVA table is presented in Table 1 (see, e.g., Box et al., *Statistics For Experimenters*, John Wiley & Sons, 1978). The ANOVA table summarizes the quantities used in ANOVA calculation.

TABLE 1

One-way traditional ANOVA

| Source of variation | Sum of squares | Degrees of freedom | Mean square |
|---|---|---|---|
| Grand average | $S_A = N \cdot \bar{y}^2$ | $v_A = 1$ | $S_A^2 = S_A / v_A$ |
| Between treatments | $S_T = \sum_{t=1}^{k} n_t \cdot (\bar{y}_t - \bar{y})^2$ | $v_T = k - 1$ | $S_T^2 = S_T / v_T$ |
| Within treatments | $S_R = \sum_{t=1}^{k} \sum_{i=1}^{n_t} (y_{ti} - \bar{y}_t)^2$ | $v_R = N - k$ | $S_R^2 = S_R / v_R$ |
| Total between and within | $S_{RT} = S_R + S_T$ | $v_{RT} = N - 1$ | |
| Total | $S = \sum_{t=1}^{k} \sum_{i=1}^{n_t} y_{ti}^2$ | N | |

In the traditional ANOVA, the statistical metric for F-statistics can be the ratio of the estimated mean squares in Table 1, i.e., $S_T^2/S_R^2$. The probability that the null-hypothesis may be accepted using an F-test is then calculated as a p-value according to Equation 33. When the p-value is lower than a given threshold, for example p-value<0.01, the null-hypothesis is rejected and the alternative hypothesis $H_1$ is accepted.

$$p\text{value} = 1 - fcdf(s_T^2/s_R^2, v_T, v_R) \qquad (33)$$

Other statistical tests can also be used in ANOVA. A skilled person in the art will be able to select a suitable statistical test based on, e.g., the type of data to be analyzed and the goal of the analysis (see, e.g., Wu et al., "MAANOVA: A software package for the Analysis of Spotted cDNA Microarray Experiments," published on the web, which is incorporated by reference herein in its entirety).

5.3.2. Improved ANOVA Methods

The invention provides an improved ANOVA method for analyzing measurement data. In the improved ANOVA method of the invention, for each measurement $y_{ti}$ of a biological variable y, in addition to the measurement quantity $y_{ti}$ itself, e.g., measured expression level of a gene, a second input is also used. The second input is a predetermined measurement variance or error. In the present invention, a predetermined measurement variance or error can be any variance or error which is determined prior to the ANOVA analysis. For example, the predetermined variance or error of a measurement can be determined based on measured data which are obtained either prior to or concurrently with the measurements to be analyzed. In one embodiment, the predetermined variance or error of a measurement of a variable is determined based on prior measurements of the same variable using the same measurement technological platform, e.g., prior measurements of the expression level of the same gene or protein using the same type of microarrays. In another embodiment, the predetermined variance or error of a measurement of a variable is determined based on concurrent measurements of a plurality of different variables using the same measurement technological platform, e.g., measurements of the expression levels of a plurality of different genes using one or more microarrays. The plurality of different variables may include the variable whose predetermined variance or error is to be determined. Alternatively, the plurality of different variables may include only variables other than the variable whose predetermined variance or error is to be determined. The predetermined error or variance can be determined from such prior or concurrent measurements using a suitable error model. Determination of the predetermined variance or error based on a combination of the above discussed prior and concurrent measurements is also envisioned. In this disclosure, a predetermined measurement variance or error is also referred to as a "prior," which is intended to encompass a predetermined variance or error determined by any of the methods disclosed above. In one embodiment, the additional input is an estimated standard error of the measurement $y_{ti}$, $\sigma_{ti}$.

In preferred embodiments, the invention provides a method of analyzing a plurality of measurements of a variable $\{y_{ti}\}$ in k different measurement groups, where $y_{ti}$ is the ith measurement in the tth measurement group, $t=1, 2, \ldots, k$ and $i=1, 2, \ldots, n_t$, $n_t$ being the number of measurements in measurement group t. Each of the k different measurement groups consists of measurements of the variable under a particular condition or perturbation common to the measurement group. Each measurement $y_{ti}$ has a predetermined measurement variance. In the method of the invention, each measurement $y_{ti}$ is first weighted with a weighting factor to obtain an error-weighted measurement. The weighting factor can be determined based on the measurement variance of the measurement. In one embodiment the weighting factor is calculated according to Equation (34), infra. Then a within-group variance for the k different measurement groups is determined. The within-group variance consists of a propagated variance and a scattered variance. The propagated variance can be determined based on the predetermined measurement variances of the plurality of measurements, and the scattered variance can be determined based on deviation of each of the plurality of measurements with respect to a respective group mean, i.e., a mean of error-weighted measurements in a respective measurement group. It will be apparent to one skilled in the art that if a measurement group contains only one measurement, the mean is the same as the measurement. In a preferred embodiment, the propagated variance for each measurement group is determined according to Equation (37), infra. In another preferred embodiment, the scattered variance is determined according to Equation (40), infra. A between-group variance for said k different measurement groups is then determined. The between-group variance is a variance of a plurality of group means, one for each of the k different measurement groups, with respect to a mean of the plurality of error-weighted measurements. The within-group variance is then compared with the between-group variance to determine, e.g., if the condition or perturbation has an effect on the variable.

The method of the invention can also be carried out without error-weighting the measurements. In such a method, a within-group variance for the k different measurement groups is determined. The within-group variance consists of a propagated variance and a scattered variance. The propagated variance can be determined based on the measurement variances of the plurality of measurements, and the scattered variance can be determined based on deviation of each of the plurality of measurements with respect to a respective group mean, i.e., a mean of measurements in a respective measurement group. It will be apparent to one skilled in the art that if a measurement group contains only one measurement, the mean is the same as the measurement. In a preferred embodiment, the propagated variance for each measurement group is determined according to Equation (37a), infra. In another preferred embodiment, the scattered variance is determined according to Equation (40a), infra. A between-group variance for said k different measurement groups is then determined. The between-group variance is a variance of a plurality of group means, one for each of the k different measurement groups, with respect to a mean of the plurality of error-weighted measurements. The within-group variance is then compared with the between-group variance to determine, e.g., if the condition or perturbation has an effect on the variable.

In a preferred embodiment, the within-group variance is a sum of a plurality of group variances, each of which consisting of a measurement group propagated variance and a measurement group scattered variance. The measurement group propagated variance can be determined based on the predetermined measurement variances of the one or more measurements in the measurement group. The measurement group scattered variance is a variance of the one or more measurements with respect to the mean of the one or more measurements or error-weighted measurements in the measurement group. It will be apparent to one skilled in the art that if a measurement group contains only one measurement, the mean is the same as the measurement. In a preferred embodiment, the mean of said error-weighted measurement is determined according to Equation (36), infra, and the scattered variance is determined according to Equation (40), infra.

The propagated variance and the scattered variance are preferably combined in such a manner that when the number of measurements in a measurement group is small, the propagated error is dominant, whereas when the number of measurements in a measurement group increases, the scattered error becomes more and more dominant, and when the number of measurements in a measurement group become very large, the group variance approaches the scattered error. In another preferred embodiment, the propagated variance and the scattered variance are combined according to Equation (43), infra.

In one embodiment, the comparison of the within-group variance and the between-group variance is carried out using an appropriate statistical test, e.g., an F-test. In such an embodiment, within-group degree of freedom, between-group degree of freedom, within-group mean square, and between-group mean square are first determined using the appropriate variances. In a preferred embodiment, these parameters are determined according to the respective equations in Table 2. A significance level, e.g., a p-value, can then be determined, e.g., according to Equation (33).

In another embodiment, the analysis can be carried out by applying traditional ANOVA on error-weighted measurements.

In a preferred embodiment, a technology platform specific error model is used to determine the predetermined measurement error $\sigma_{ti}$. Such estimated measurement error is used as a predetermined error or a "prior" in the within-group variance estimation. In a more preferred embodiment, the errors are estimated using an error model described in Section 5.2., supra. Preferably, the additional input $\sigma_{ti}$ comes from an application-specific error model, e.g., a three term error model as described by Equation 8. Based on the knowledge of data noise sources and training data, the error model provides a conservative estimation of the measurement error in quantity y. Measurement error contains errors from various sources, including sample preparation (inverse-transcription, amplification, et al), labeling and dye related bias, hybridization, chip quality variation, chip scanning and image feature extraction. The measurement error determines the lower bound of the total error that includes biological variations. When the number of replicates is limited, the measurement error can be used as a "prior" in the variance estimation. The measurement error provides additional information to obtain better variance estimations. The additional input also brings in additional degrees-of-freedom in the analysis. Both the improved variance estimation and the additional degree-of-freedom can help increase the statistical power of the analysis. The measurement error may also be used for determining the quality of the measurement. Weights that are inversely proportional to measurement errors in the mean estimation may be used to penalize measurements with large errors.

In another embodiment, a common error in an experiment estimated across a plurality of different biological variables y's measured in the same experiment, e.g., expression levels of different genes measured by using one or more microarrays in an experiment, is used to determine the measurement error for one or more of the measurements of y's. In a more preferred embodiment, such a common error is estimated according the method disclosed in U.S. Pat. No. 6,351,712, which is incorporated herein by reference in its entirety. Common errors determined by other methods can also be used (See, Section 5.3.2.5, infra).

The invention is based, at least in part, on the discovery by the inventor that when the number of replicate measurements in one or more measurement groups is small, the second input provides for more reliable variance estimation. Therefore, the additional input may help setting a "floor" in the within-group variance estimations for more accurate determination of the within-group variance. The additional input may also provide additional degrees-of-freedom to the analysis. As a result, both false-positive and false negative rates may be significantly reduced.

In addition, the additional input, e.g., the measurement error $\sigma_{ti}$, can be used in error-weighted averaging for the group mean estimation. In one embodiment, the weight is inversely proportional to the square of $\sigma_{ti}$ so that measurements with larger errors will have less contribution to the mean estimation.

The improved ANOVA methods of the invention can be used to carry out analysis of any measurements, including but not limited to intensity data, such as gene expression intensity data obtained using Affymetrix micro-arrays, and ratio data, such as gene expression ratio data obtained using Agilent micro-arrays.

5.3.2.1. Error-Weighted Average

In traditional ANOVA, the grand average and the treatment-group average are computed using Eqs. 31 and 32. In such calculations, all measurements are treated equally. This is equivalent to assign one as the weight to all data points. If it is known a priori that some data points have larger measurement errors than others, it may be desirable to give them smaller weights in the calculation of the average to minimize their impacts to the accuracy of the mean estimation.

In a preferred embodiment, the weighting factor can be defined as:

$$w_{ti} = \frac{1}{\sigma_{ti}^2} \qquad (34)$$

where $\sigma_{ti}$ is standard error of the measurement. It will be apparent to an ordinary skilled person in the art that other error may also be used to define the weighting factor In this embodiment, the grand average and the treatment group average are calculated as:

$$\bar{y} = \frac{\sum_{t=1}^{k} \sum_{i=1}^{n_t} w_{ti} \cdot y_{ti}}{\sum_{t=1}^{k} \sum_{i=1}^{n_t} w_{ti}}, \qquad (35)$$

and $$\bar{y}_t = \frac{\sum_{i=1}^{n_t} w_{ti} \cdot y_{ti}}{\sum_{i=1}^{n_t} w_{ti}}, \qquad (36)$$

respectively.

The propagated errors of the weighted treatment group average and the grand average are calculated as $$\sigma_{\bar{y}_t P}^2 = \frac{1}{\sum_{i=1}^{n_t} w_{ti}} = \frac{1}{\sum_{i=1}^{n_t} \frac{1}{\sigma_{ti}^2}}, \qquad (37)$$

and $$\sigma_{\bar{y}P}^2 = \frac{1}{\sum_{t=1}^{k} \sum_{i=1}^{n_t} w_{ti}} = \frac{1}{\sum_{t=1}^{k} \sum_{i=1}^{n_t} \frac{1}{\sigma_{ti}^2}} = \frac{1}{\sum_{t=1}^{k} \frac{1}{\sigma_{\bar{y}_t P}^2}} = \frac{1}{\sum_{t=1}^{k} w_t}, \qquad (38)$$

respectively, where a treatment group weight is defined as $$w_t = \frac{1}{\sigma_{\bar{y}_t P}^2} \qquad (39)$$

The scattered errors of the weighted treatment group average and the grand average are calculated as $$\sigma_{\bar{y}_t s}^2 = \frac{1}{(n_t - 1) \cdot \sum_{i=1}^{n_t} w_{ti}} \cdot \sum_{i=1}^{n_t} w_{ti} \cdot (y_{ti} - \bar{y}_t)^2 \qquad (40)$$

and $$\sigma_{\bar{y}s}^2 = \frac{1}{(N - 1) \cdot \sum_{t=1}^{k} \sum_{i=1}^{n_t} w_{ti}} \cdot \sum_{t=1}^{k} \sum_{i=1}^{n_t} w_{ti} \cdot (y_{ti} - \bar{y})^2 \qquad (41)$$

respectively.

The propagated error provides prior information for the error estimation. In a preferred embodiment, the error model as described in Section 5.2, supra, is used to estimate the propagated error for each y. In another embodiment, the propagated error and the scattered error are combined to improve error estimation for the group average and the grand average. The combination idea is that when the number of samples is small the prior should contribute more to the combined error estimation, whereas when the number of samples becomes large, the combined error should be dominated by the scattered error, which is the actual error estimation from data. In the case of large number of samples, the estimated error becomes less dependent on the error model. The weight is defined as inversely proportional to the variance of the error of the scattered error. In one embodiment, because the error of the scattered error is $$\sigma_{\sigma_{\bar{y}_t s}} = \frac{\sigma_{\bar{y}_t s}}{\sqrt{2 \cdot (n_t - 1)}} \quad (42)$$

a weight that is proportional to 2(n−1) is used to weight the scattered error. It is also known that the sum of all weights should be equal to one. The total error of the treatment-group average and the total error of the grand average are calculated as $$\sigma_{\bar{y}_t} = \frac{2 \cdot \sigma_{\bar{y}_t P} + 2 \cdot (n_t - 1) \cdot \sigma_{\bar{y}_t s}}{2 \cdot n_t} = \frac{\sigma_{\bar{y}_t P} + (n_t - 1) \cdot \sigma_{\bar{y}_t s}}{n_t} \quad (43)$$

and $$\sigma_{\bar{y}} = \frac{\sigma_{\bar{y}P} + (N - 1) \cdot \sigma_{\bar{y}s}}{N} \quad (44)$$

respectively.

In another embodiment, in the method that does not involve error-weighting the measurements, the Eqs. 35-38 and 40-41 are replaced respectively with the following equations, $$\bar{y} = \frac{\sum_{t=1}^{k} \sum_{i=1}^{n_t} y_{ti}}{N}. \quad (35a)$$

$$\bar{y}_t = \frac{\sum_{i=1}^{n_t} y_{ti}}{n_t}. \quad (36a)$$

$$\sigma_{\bar{y}_t P}^2 = \frac{\sum_{i=2}^{n_t} \sigma_{ti}^2}{n_t^2}, \quad (37a)$$

$$\sigma_{\bar{y}P}^2 = \frac{\sum_{t=1}^{k} \sum_{i=1}^{n_t} \sigma_{ti}^2}{N^2}, \quad (38a)$$

$$\sigma_{\bar{y}_t s}^2 = \frac{1}{(n_t - 1)} \cdot \sum_{i=1}^{n_t} (y_{ti} - \bar{y}_t)^2, \quad (40a)$$

$$\sigma_{\bar{y}s}^2 = \frac{1}{(N - 1)} \cdot \sum_{t=1}^{k} \sum_{i=1}^{n_t} (y_{ti} - \bar{y})^2. \quad (41a)$$

5.3.2.2. Improved Mean-Square Estimation

In Table 1, when the within-group degrees-of-freedom N-k is small, the error of within-group mean-square is large. The error of the mean-square estimation is inversely proportional to the square of N−k, which is the sum of degrees-of-freedom $(n_k-1)$ within the treatment group. When the number of replicates $n_k$ is small, there is less confidence in the within-group variance estimation.

In one embodiment, instead of calculating within-group mean-square using the within-group sum of squares, the within-group mean-square is calculated based on the estimated error. By definition the group mean-square is the error square multiplied by the number of samples. For treatment group t, the mean-square is calculated as $$s_{RT}^2 = n_t \cdot \sigma_{\bar{y}_t}^2 = \frac{(\sigma_{\bar{y}_t P} + (n_t - 1) \cdot \sigma_{\bar{y}_t s})^2}{n_t} \quad (45)$$

By definition, the sum of squares of group t is the group mean-square multiplied by the DOF of the group mean-square estimation:

$$S_{Rt} = v_{Rt} s_{Rt}^2 \quad (46)$$

where the group degree-of-freedom (DOF) is given in Section 5.3.2.3, infra.

The total sum of squares is the sum of the group sum of squares:

$$S_R = \sum_{t=1}^{k} v_{Rt} \cdot s_{RT}^2 = \sum_{t=1}^{k} \left[ v_{Rt} \cdot \frac{(\sigma_{\bar{y}_t P} + (n_t - 1) \cdot \sigma_{\bar{y}_t s})^2}{n_t} \right] \quad (47)$$

By definition, the overall mean square is the total sum of squares divided by the total within-group DOF:

$$s_R^2 = \frac{S_R^2}{v_R} \quad (48)$$

where the total DOF is given in Section 5.3.2.3, infra.

In one embodiment, if a prior for the between-treatment variance that depends on the treatments is not available, the same estimation method as shown in Table 1 is used to estimate the between-treatment variance. In another embodiment, if a prior for the between-treatment variance is available, the between-treatment variance is obtained by a combination of a propagated error and a scattered error in a manner similar to the within-treatment variance as described in Section 5.2.2.1, supra.

The first error term in Equations 43 and 44 reflects the propagated measurement errors of the derived averages. In one embodiment, this error term is defined in Equation 37. It is used as prior in the mean square estimation to improve the estimation accuracy especially when the number of replicates is small. When the number of replicates is small, by mere random chances, the sum-squares without the priors can be much larger or smaller than the inherent measurement error in the measurement technology, e.g., the microarray technology, resulting in high false-negative rate and false-positive rate, respectively. The prior sets a floor in the sum-square estimation so that the estimation can not become unreasonably small. The new measurement-error input provides additional prior information to help improve the power of ANOVA analysis.

5.3.2.3. Additional Degrees-Of-Freedom

The additional measurement-error input also brings in more degrees-of-freedom to the ANOVA analysis. The additional within-treatment DOF gained from the additional ANOVA input can be determined based on the level of confidence of the predetermined variance or error. The additional DOF can range from zero, if the level of confidence of the predetermined variance or error is low, to a large number, if the level of confidence of the predetermined variance or error is high. For example, the within-treatment DOF can be assigned to a very large number (e.g., at least 20, 50, or 100) regardless of the number of measurements in the measurement groups, if the predetermined variance or error is already a conservative and realistic estimation of the measurement error. The level of confidence of the predetermined variance or error can be determined based on the manner such variance or error is obtained (see, e.g., e.g., Stoughton et al., U.S. Pat. No. 6,351,712, which is incorporated by reference herein in its entirety).

In a preferred embodiment, from the propagated error in Equation 37 and the scattered error in Equation 40, the within-treatment DOF of the propagated error is calculated as $$v_{\bar{y}_t p} = n_t \tag{49}$$

and the within-treatment DOF of the scattered error is $$v_{\bar{y}_t s} = n_t - 1 \tag{50}$$

In a preferred embodiment, the two errors are weighted when estimating the individual mean-square of treatment group t in Equation 45. Each error has reduced contribution to the combined result, so does its DOF. The DOF of the group mean-square is the weighted combination of the DOF's of the two individual error terms:

$$v_{Rt} = \frac{(n_t - 1) \cdot v_{\bar{y}_t p} + (n_t - 1) \cdot v_{\bar{y}_t s}}{n_t} = \frac{(n_t - 1) \cdot (n_t - 1)}{n_t} = n_t - 1 + \frac{1}{n_t} \tag{51}$$

Based on Equation 47, the total within-treatment DOF is the sum of DOF's of all individual group:

$$v_R = \sum_{t=1}^{k} v_{Rt} = \sum_{t=1}^{k} \left( n_t - 1 + \frac{1}{n_t} \right) = N - k + \sum_{t=1}^{k} \frac{1}{n_t} \tag{52}$$

It can be seen that the within-treatment DOF as described by Equation 52 is increased as compared to the value in Table 1. The higher degrees-of-freedom provide more statistical power to the ANOVA analysis and therefore higher sensitivity.

When the error-weighting method is used to compute the averages and their errors, for example using Equations 36, 37 and 40, those data points that have large measurement errors contribute less to the mean and variance estimations. The total effective number of samples used in the calculation is therefore equal or less than the total number of actual input samples. In one embodiment, the effective numbers of samples in Table 2 are calculated as $$en_t = \left( \frac{\min(\sigma_{ti})}{\sigma_{\bar{y}_t p}} \right)^2 = (\min(\sigma_{ti}))^2 \cdot \sum_{i=1}^{n_t} w_{ti} \tag{53}$$

$$eN = \sum_{t=1}^{k} en_t. \tag{54}$$

In the embodiment that does not involve error-weighting the measurements, Eqs. 53 and 54 are replaced respectively with the following equations, $$en_t = n_t \tag{53a}$$

$$eN = N. \tag{54a}$$

Table 2 lists an exemplary embodiment of one-way improved ANOVA with error-weighting in which changes from the traditional ANOVA (Table 1) can be easily seen. In the embodiment that does not involve error-weighting the measurements, the equations in Table 2 can be modified by substituting the relevant quantities, e.g., the averages, variances, and effective number of samples, with the quantities calculated using Eqs. 35a-38a, 40a-41a, and 53a-54a.

In one embodiment, F-statistics is used to test the null-hypothesis. For example, the statistical metric can be calculated using the mean squares and DOFs of Table 2, and the ANOVA p-value can be calculated using Equation 33. It will be apparent to one skilled in the art that any other statistical tests, e.g., t-test, in which the estimation of variance within treatment replicates is used for determining the statistical metric may also be used in the present invention.

TABLE 2

| An Exemplary Embodiment of Improved One-way ANOVA | | | |
|---|---|---|---|
| Source of variation | Sum of squares | Degrees of freedom | Mean square |
| Grand average | $S_A = eN \cdot \bar{y}^2$ | | |
| Grand average error | $S_E = eN \cdot \sigma_{\bar{y}}^2$ | | |
| Between treatments | $S_T = \sum_{t=1}^{k} en_t \cdot (\bar{y}_t - \bar{y})^2$ | $v_T = k - 1$ | $S_T^2 = S_T / v_T$ |
| Within treatments | $S_R = \sum_{t=1}^{k} \left[ v_{Rt} \cdot \frac{(\sigma_{\bar{y}_t p} + (en_t - 1) \cdot \sigma_{\bar{y}_t s})^2}{en_t} \right]$ | $v_R = eN - k + \sum_{t=1}^{k} \frac{1}{en_t}$ | $S_R^2 = S_R / v_R$ |

TABLE 2-continued

An Exemplary Embodiment of Improved One-way ANOVA

| Source of variation | Sum of squares | Degrees of freedom | Mean square |
|---|---|---|---|
| Total between and within | $S_{RT} = S_R + S_T$ | $v_{RT} = eN - 1 + \sum_{t=1}^{k} \frac{1}{en_t}$ | |

5.3.2.4. Improved Two-Way ANOVA

The invention also provides improved two-way and N-way ANOVA for analyzing measured and/or transformed data under two or more different conditions, e.g., perturbations. For simplicity, 2-way improved ANOVA is described in this section. It will be apparent to a person skilled in the art that N-way improved ANOVA can be practiced similarly. The notation used is similar to those used in Box et al., *Statistics For Experimenters*, John Wiley & Sons, 1978.

If there are two factors P having n levels, denoted as i, where i can be from 1 to n, and T having k levels, denoted as t, where t can be from 1 to k; and if the number of replicates in group ti is $m_{ti}$, each replicate is denoted by as j, i.e., the index for the replicates is j, wherein j can be from 1 to $m_{ti}$, the relevant quantities for the traditional 2-way ANOVA are summarized in Table 3. The total number of samples and the grand average are $$N = \sum_{t=1}^{k} \sum_{i=1}^{n} m_{ti}, \quad (55)$$

and $$\overline{y} = \frac{1}{N} \sum_{t=1}^{k} \sum_{i=1}^{n} \sum_{j=1}^{m_{ti}} y_{tij}, \quad (56)$$

respectively. The number of samples for Factor P and Factor T are $$N_i = \sum_{t=1}^{k} m_{ti}, \quad (57)$$

and $$N_t = \sum_{i=1}^{n} m_{ti}, \quad (58)$$

respectively. Group averages for Factor P and Factor T are $$\overline{y}_i = \frac{\sum_{t=1}^{k} \sum_{j=1}^{m_{ti}} y_{tij}}{N_i}, \quad (59)$$

and $$\overline{y}_t = \frac{\sum_{i=1}^{n} \sum_{j=1}^{m_{ti}} y_{tij}}{N_t}, \quad (60)$$

respectively. The interaction average is $$\overline{y}_{ti} = \frac{\sum_{j=1}^{m_{ti}} y_{tij}}{m_{ti}}. \quad (61)$$

TABLE 3

Traditional Two-way ANOVA Table

| Source of variation | Sum of squares | Degrees of freedom | Mean square |
|---|---|---|---|
| Grand average | $S_A = N \cdot \overline{y}^2$ | $v_A = 1$ | $S_A^2 = S_A / v_A$ |
| Between treatment P | $S_P = \sum_{i=1}^{n} N_i \cdot (\overline{y}_i - \overline{y})^2$ | $v_P = n - 1$ | $S_P^2 = S_P / v_P$ |
| Between treatment T | $S_T = \sum_{t=1}^{k} N_t \cdot (\overline{y}_t - \overline{y})^2$ | $v_T = k - 1$ | $S_T^2 = S_T / v_T$ |
| P-T Interaction | $S_I = \sum_{t=1}^{k} \sum_{i=1}^{n} m_{ti} \cdot (\overline{y}_{ti} - \overline{y}_t - \overline{y}_i + \overline{y})^2$ | $v_I = (n - 1) \cdot (k - 1)$ | $S_I^2 = S_I / v_I$ |
| Within treatments (error) | $S_R = \sum_{t=1}^{k} \sum_{i=1}^{n} \sum_{j=1}^{m_{ti}} (y_{tij} - \overline{y}_{ti})^2$ | $v_R = \sum_{t=1}^{k} \sum_{i=1}^{n} (m_{ti} - 1) = N - n \cdot k$ | $S_R^2 = S_R / v_R$ |

The invention therefore provides an improved two-way ANOVA method for analyzing a plurality of measurements of a variable in a plurality of different measurement groups, each of which consisting of one or more measurements of the variable under a condition among a first plurality of conditions and a condition among a second plurality of conditions, and each measurement has a predetermined measurement variance. The improvement comprises determining a within-group variance consisting of a propagated variance and a scattered variance. The propagated variance can be determined based on the predetermined measurement variances of the plurality of measurements, and the scattered variance is determined based on deviation of each of the plurality of measurements with respect to a mean of measurements in a respective measurement group.

In one embodiment, the averages or error-weighted averages, propagated and scattered errors, DOF's, and effective number of samples for improved two-way ANOVA are similarly derived as those for the improve one-way ANONA (Sections 5.3.2.2-5.3.2.4). For example, the within-treatment DOF of group ti is $$v_{Rti} = m_{ti} - 1 + \frac{1}{m_{ti}}. \tag{62}$$

As another example, the within-treatment effective number of samples is $$em_{ti} = \left(\frac{\min(\sigma_{tij})}{\sigma_{\bar{y}_{ij}P}}\right)^2 = (\min(\sigma_{tij}))^2 \cdot \sum_{j=1}^{m_{ti}} w_{tij}, \tag{63}$$

In one embodiment, the invention provides a method of analyzing a plurality of measurements of a variable $\{y_{tij}\}$ in k*n different measurement groups, where $y_{tij}$ is the jth measurement in the tith measurement group, t=1, 2, ..., n, i=1, 2, ..., and k, j=1, ..., $m_{ti}$, $m_{ti}$ being the number of measurements in measurement group ti. Each of the k*n different measurement groups consists of measurements of the variable under conditions t and i of condition groups N having n different conditions and K having k different conditions, respectively. Each measurement $y_{tij}$ has a predetermined measurement variance. In the method of the invention, each measurement $y_{tij}$ is first weighted with a weighting factor to obtain an error-weighted measurement. The weighting factor can be determined based on the predetermined measurement variance of the measurement. In one embodiment the weighting factor is calculated according to Equation (34). A within-group variance for the k*n different measurement groups is then determined. The within-group variance consists of a propagated variance and a scattered variance. The propagated variance can be determined based on the predetermined measurement variances of the plurality of measurements, and the scattered variance can be determined based on deviation of each of the plurality of measurements with respect to a mean of measurements in a respective measurement group. In a preferred embodiment, the propagated variance for each measurement group is determined according to Equation (37). In another preferred embodiment, the scattered variance is determined according to Equation (40). Then a between-group variance for condition group K or N, or for interaction between condition groups K and N is determined. The within-group variance is then compared with the between-group variance to determine, e.g., if either of two groups of conditions have effects on the variable. In one embodiment, the effect of condition group K is determined using the between-group variance of condition group K which is a variance of the group means for the respective conditions in condition group K with respect to a mean of the plurality of error-weighted measurements. Each group mean for a condition in condition group K is the mean of measurements in all measurement groups under a respective condition in condition group K. The effect of condition group N can be determined in a similar way by using the between-group variance of condition group N which is a variance of the group means for the respective conditions in condition group N with respect to a mean of the plurality of error-weighted measurements, where each group mean for a condition in condition group N is the mean of measurements in all measurement groups under a respective condition in condition group N. The effect of the interaction between condition group N and condition group K can also be determined using the interaction variance which is a variance of group interaction means with respect to the mean of the plurality of error-weighted measurements and the condition group mean for condition group K and the condition group mean for condition group N, where each group interaction mean is the mean of measurements in a measurement group over the number of measurements in the measurement group, e.g., as calculated by the equations in Table 4. The method is also applicable to error-weighted measurements.

Table 4 summarizes the quantities in an exemplary embodiment of improved 2-way NOVA. As can be seen from Table 4, in addition to error-weighted averaging and effective number of samples, the within-treatment sum of squares and DOFs are also changed as compared to the traditional ANOVA.

TABLE 4

Improved Two-way ANOVA Table

| Source of variation | Sum of squares | Degrees of freedom | Mean square |
| --- | --- | --- | --- |
| Grand average | $S_A = eN \cdot \bar{y}^2$ | $v_A = 1$ | $S_A^2 = S_A / v_A$ |
| Between treatment P | $S_P = \sum_{i=1}^{n} eN_i \cdot (\bar{y}_i - \bar{y})^2$ | $v_P = n - 1$ | $S_P^2 = S_P / v_P$ |
| Between treatment T | $S_T = \sum_{t=1}^{k} eN_t \cdot (\bar{y}_t - \bar{y})^2$ | $v_T = k - 1$ | $S_T^2 = S_T / v_T$ |

TABLE 4-continued

Improved Two-way ANOVA Table

| Source of variation | Sum of squares | Degrees of freedom | Mean square |
|---|---|---|---|
| P-T Interaction | $S_I = \sum_{t=1}^{k} \sum_{i=1}^{n} em_{ti} \cdot (\bar{y}_{ti} - \bar{y}_t - \bar{y}_i + \bar{y})^2$ | $\nu_I = (n-1) \cdot (k-1)$ | $S_I^2 = S_I / \nu_I$ |
| Within treatments (error) | $S_R = \sum_{t=1}^{k} \sum_{i=1}^{n} \left[ \nu_{Rti} \cdot \frac{(\sigma_{\bar{y}_{ti}P} + (em_{ti} - 1) \cdot \sigma_{\bar{y}_{ti}s})^2}{em_{ti}} \right]$ | $\nu_R = eN - n \cdot k + \sum_{t=1}^{k} \sum_{i=1}^{n} \frac{1}{m_{ti}}$ | $S_R^2 = S_R / \nu_R$ |

It will be apparent to a skilled person in the art that improved N-way ANOVA can be obtained by, e.g., properly introducing more indices and computing the appropriate ANOVA table.

5.3.2.5. Other Measurement Errors as ANOVA Inputs

Measurement variance $\sigma_{ti}$ can also be determined by various other methods known in the art and used as the additional ANOVA input. The methods of the invention are equally applicable to such measurement variance. For example, the methods as described in Sections 5.3.3.1. through 5.3.3.5 can be used in conjunction with such measurement variance. In one embodiment, common error variance associated with an experiment estimated across a plurality of different biological variables measured in the experiment is used as the measurement error $\sigma_{ti}$. The number of the plurality of different biological variables used for determining the common errors can be chosen by one skilled person in the art. In preferred embodiments, the number is at least 2, 5, 10, 100, 1000, or 10,000. For example, in a microarray experiment, common error variance across a plurality of different genes measured on a microarray can be used as the additional input in the improved ANOVA method of the invention for one or more genes in the plurality of different genes. Such common error can be estimated over more than one replicates of the experiment, e.g., more than one replicates of a microarray experiment. In a preferred embodiment, such a common error is estimated from one or more replicates according a method disclosed in U.S. Pat. No. 6,351,712, which is incorporated herein by reference in its entirety. In another embodiment, the error estimation may come from a regression analysis. In one embodiment using regression analysis, the relationship between intensity and intensity error can be find by fitting a function to the data set of one or several replicates. Error variance across a plurality of control or reference probes on a microarray can also be used as the additional input in the improved ANOVA method of the invention. It will be apparent to one skilled in the art that measurement variance determined by any other suitable method can also be used as the additional ANOVA input.

5.4. Other Applications of Improved ANOVA

The invention also provides method of using the improved ANOVA for determining if measured data are unchanged under different conditions or perturbations and for determining if replicate measurements in a group are consistent with each other.

5.4.1. Method of Determining Unchanged Measurements

Measurements for which the null-hypothesis cannot be rejected, e.g., determined by ANOVA as not different under different conditions or perturbations, are not necessarily unchanged. For example, although an ANOVA analysis of measured expression levels of a gene or protein under a set of different drug treatments indicates that the expression of the gene or protein is not changed under the set of treatments, the expression levels may nonetheless have changed under some circumstances. This is due to the fact that there are several factors that may affect an ANOVA test. One possibility that a null-hypothesis can not be rejected is that the null is indeed true where treatment groups do have the same mean. Another possibility that a null-hypothesis cannot be rejected is that the within-group variance is too large. For genes or proteins whose expression levels have high ANOVA p-value (e.g. p-value>0.95), if they also have small within-group variances, it may be expected that they are unchanged.

The invention therefore provides, in one embodiment, a method of determining if measured data of a biological variable under different conditions or perturbations have a large or small within-group variance. The method of the invention makes use of the average within-group mean-square determined across a plurality of different biological variables, and compares the individual mean-square of measurements of the biological variable of interests with the average. The hypothesis is that the individual mean-square is smaller than the average. If the hypothesis can be accepted, e.g., by an appropriate statistical test, the within-group variance is deemed small. For example, in a microarray experiment, a plurality of different genes are measured under a set of different conditions or perturbations, each on one or more microarrays. In one embodiment, if M is the number of different biological variables, e.g., the total number of measurements in each gene or protein expression profile, and $s_R^2(j)$ is the within-group mean-square of the j'th biological variables, the average within-group mean-square is defined as:

$$\bar{s}_R^2 = \frac{1}{M} \cdot \sum_{j=1}^{M} s_R^2(j). \tag{64}$$

Preferably, M is at least 2, 5, 10, 50, 100, 1000, 10,000 or 100,000. The different biological variables used for calculating the average can also be selected if desired. For example, data generated from bad array spots can be excluded. The individual within-group mean-square is then compared with the average in an F-test as described by Eq. 65, where the DOF of the average $v_{avg}$ is typically large. In one embodiment, the DOF of $v_{avg}$ is set to a large arbitrary number in the computation because the Chi-Square distribution of the average is approaching a Gaussian distribution when the DOF is large. The within-group variance of the ith biological variable can be compared with the average within-group variance using Eq. (65)

$$\text{SmallError\_pvalue}(i)=1-fdcf(s_R^2(i)/\bar{s}_R^2, v_R, v_{avg}). \quad (65)$$

When SmallError_pvalue(i) is large, the individual within-group mean-square of the ith biological variable is identified as smaller than the average mean-square. In a preferred embodiment, the SmallError_pvalue threshold is set to be greater than 0.5, thus, those biological variables/measurements that have within-group mean-squares less than the average are accepted as having small within-group variance. In a preferred embodiment, the within-group mean squares in Eqs. 64 and 65 are calculated using the improved ANOVA method of the invention, e.g., according to Table 2 or Table 4.

In one embodiment, to detect unchanged biological variables/measurements, two p-value thresholds, one for the ANOVA p-value and one for the SmallError p-value, are set. In a preferred embodiment, the ANOVA p-value is determined using a method of the invention as described in Section 5.3. Biological variables/measurements which have the ANOVA p-value and the SmallError p-value greater than the respective threshold are determined as truely unchanged. In a preferred embodiment, the thresholds are selected as the ANOVA p-value>0.95 and the SmallError p-value>0.5. It will be apparent to one skilled in the art that other thresholds for the ANOVA p-value and the SmallError p-value can also be selected according to particular experimental conditions. In another preferred embodiment, the thresholds are selected as the ANOVA p-value>0.95 and the SmallError p-value>0.9.

5.4.2. Method of Analyzing Variations Among Replicate Measurements

The invention also provides a method of using the improved ANOVA method for detecting variations among replicates in a treatment group, thereby determining the consistency of the replicates.

In one embodiment, for a given variable j in treatment group t, an F-test is used to compare the scattered error as determined according to Equation 40 (Equation 40a if the measurements are not error weighted) and the propagated error as determined according to Equation 37 (Equation 37a if the measurements are not error weighted). If the scattered error is significantly larger than the propagated error, it indicates there are variations beyond measurement error. In one embodiment, a p-value of this F-test, termed "replicate consistency p-value" is calculated as:

$$\text{Consistency\_pvalue}(j) = \quad (66)$$
$$1 - fcdf\big((en_t(j) \cdot \sigma_{\bar{y}_t,s}^2(j))/(en_t(j) \cdot \sigma_{\bar{y}_t P}^2(j)), en_t(j) - 1,$$
$$en_t(j)\big) = 1 - fcdf\big(\sigma_{\bar{y}_t,s}^2(j)/\sigma_{\bar{y}_t P}^2(j), en_t(j) - 1, en_t(j)\big)$$

A threshold is selected for the replicate consistency p-value. If the percentage of the number of biological variables/measurements having the p-value below the threshold to the total number of biological variables/measurements measured is significantly above the threshold level, it indicates the inconsistency among replicates in this treatment group. In a preferred embodiment, the threshold of the p-value is chosen to be less than 1% (0.01).

In one embodiment, variations in replicates beyond a level due to measurement errors are used to indicate quality issues in the data generating process. In another embodiment, when replicates are obtained from measurements of samples from different sources, e.g., a type of cell from different animals, variations in replicates beyond a level due to measurement errors are used to indicate/identified biological variations from the different sources, e.g., a type of cell from different animals.

5.5. Implementation Systems and Methods

The analytical methods of the present invention can preferably be implemented using a computer system, such as the computer system described in this section, according to the following programs and methods. Such a computer system can also preferably store and manipulate measured data obtained in various experiments that can be used by a computer system implemented with the analytical methods of this invention. Accordingly, such computer systems are also considered part of the present invention.

An exemplary computer system suitable for implementing the analytic methods of this invention is illustrated in FIG. 2. Computer system 201 is illustrated here as comprising internal components and as being linked to external components. The internal components of this computer system include one or more processor elements 202 interconnected with a main memory 203. For example, computer system 201 can be an Intel Pentium®-based processor of 200 MHZ or greater clock rate and with 32 MB or more main memory. In a preferred embodiment, computer system 201 is a cluster of a plurality of computers comprising a head "node" and eight sibling "nodes," with each node having a central processing unit ("CPU"). In addition, the cluster also comprises at least 128 MB of random access memory ("RAM") on the head node and at least 256 MB of RAM on each of the eight sibling nodes. Therefore, the computer systems of the present invention are not limited to those consisting of a single memory unit or a single processor unit.

The external components can include a mass storage 204. This mass storage can be one or more hard disks that are typically packaged together with the processor and memory. Such hard disk are typically of 1 GB or greater storage capacity and more preferably have at least 6 GB of storage capacity. For example, in a preferred embodiment, described above, wherein a computer system of the invention comprises several nodes, each node can have its own hard drive. The head node preferably has a hard drive with at least 6 GB of storage capacity whereas each sibling node preferably has a hard drive with at least 9 GB of storage capacity. A computer system of the invention can further comprise other mass storage units including, for example, one or more floppy drives, one more CD-ROM drives, one or more DVD drives or one or more DAT drives.

Other external components typically include a user interface device 205, which is most typically a monitor and a keyboard together with a graphical input device 206 such as a "mouse." The computer system is also typically linked to a network link 207 which can be, e.g., part of a local area network ("LAN") to other, local computer systems and/or part of a wide area network ("WAN"), such as the Internet, that is connected to other, remote computer systems. For example, in the preferred embodiment, discussed above, wherein the computer system comprises a plurality of nodes, each node is preferably connected to a network, preferably an NFS network, so that the nodes of the computer system communicate with each other and, optionally, with other computer systems by means of the network and can thereby share data and processing tasks with one another.

Loaded into memory during operation of such a computer system are several software components that are also shown schematically in FIG. 2. The software components comprise both software components that are standard in the art and components that are special to the present invention. These software components are typically stored on mass storage such as the hard drive 204, but can be stored on other computer readable media as well including, for example, one or more floppy disks, one or more CD-ROMs, one or more DVDs or one or more DATs. Software component 210 represents an operating system which is responsible for managing the computer system and its network interconnections. The operating system can be, for example, of the Microsoft Windows™ family such as Windows 95, Window 98, Windows NT or Windows 2000. Alternatively, the operating software can be a Macintosh operating system, a UNIX operating system or the LINUX operating system. Software components 211 comprises common languages and functions that are preferably present in the system to assist programs implementing methods specific to the present invention. Languages that can be used to program the analytic methods of the invention include, for example, C and C++, FORTRAN, PERL, HTML, JAVA, and any of the UNIX or LINUX shell command languages such as C shell script language. The methods of the invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

Software component 212 comprises any analytic methods of the present invention described supra, preferably programmed in a procedural language or symbolic package. For example, software component 212 preferably includes programs that cause the processor to implement steps of accepting a plurality of measured data and storing the measured data in the memory. For example, the computer system can accept measured data that are manually entered by a user (e.g., by means of the user interface). More preferably, however, the programs cause the computer system to retrieve measured data from a database. Such a database can be stored on a mass storage (e.g., a hard drive) or other computer readable medium and loaded into the memory of the computer, or the compendium can be accessed by the computer system by means of the network 207.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

5.6. Methods for Determining Biological State and Biological Response

This invention provides methods for analysis of measurement errors in measured signal data, e.g., measured expression profiles, and methods for analyzing and processing of such measured signal data. The measured data can be measurements of cellular constituents in a cell or organism or responses of a cell or organism to a perturbation. The data can be measured from cell samples subject to different conditions, e.g., under different perturbations. The cell sample can be of any organism, e.g., eukaryote, mammal, primate, human, non-human animal such as a dog, cat, horse, cow, mouse, rat, Drosophila, C. elegans, etc., plant such as rice, wheat, bean, tobacco, etc., and fungi. The cell sample can be from a diseased or healthy organism, or an organism predisposed to disease. The cell sample can be of a particular tissue type or development stage or subjected to a particular perturbation (stimulus). This section and its subsections provides some exemplary methods for obtaining the measured data of cell samples. One of skill in the art would appreciate that this invention is not limited to the following specific methods for measuring the expression profiles and responses of a biological system.

5.6.1. Transcript Assays using Microarrays

This invention is particularly useful for the determination of the expression state or the transcriptional state of a cell or cell type or any other cell sample by monitoring expression profiles. One aspect of the invention provides polynucleotide probe arrays for simultaneous determination of the expression levels of a plurality of genes and methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundance ratios.

Preferably, measurement of the expression profile is made by hybridization to transcript arrays, which are described in this subsection In a preferred embodiment, the present invention makes use of "transcript arrays" or "profiling arrays". Transcript arrays can be employed for analyzing the expression profile in a cell sample and especially for measuring the expression profile of a cell sample of a particular tissue type or developmental state or exposed to a drug of interest or to perturbations to a biological pathway of interest. In another embodiment, the cell sample can be from a patient, e.g., a diseased cell sample, and preferably can be compared to a healthy cell sample.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. The microarrays are preferably small, e.g., between about 1 cm$^2$ and 25 cm$^2$, preferably about 1 to 3 cm$^2$. However, both larger and smaller arrays are also contemplated and may be preferable, e.g., for simultaneously evaluating a very large number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used in the methods and compositions of the present invention include one or more test probes, each of which has a polynucleotide sequence that is complementary to a subsequence of RNA or DNA to be detected. Each probe preferably has a different nucleic acid sequence, and the position of each probe on the solid surface of the array is preferably known. Indeed, the microarrays are preferably addressable arrays, more preferably positionally addressable arrays. More specifically, each probe of the array is preferably located at a known, predetermined position on the solid support such that the identity (i.e., the sequence) of each probe can be determined from its position on the array (i.e., on the support or surface). In some embodiments of the invention, the arrays are ordered arrays.

Preferably, the density of probes on a microarray or a set of microarrays is about 100 different (i.e., non-identical) probes per 1 $cm^2$ or higher. More preferably, a microarray used in the methods of the invention will have at least 550 probes per 1 $cm^2$, at least 1,000 probes per 1 $cm^2$, at least 1,500 probes per 1 $cm^2$ or at least 2,000 probes per 1 $cm^2$. In a particularly preferred embodiment, the microarray is a high density array, preferably having a density of at least about 2,500 different probes per 1 $cm^2$. The microarrays used in the invention therefore preferably contain at least 2,500, at least 5,000, at least 10,000, at least 15,000, at least 20,000, at least 25,000, at least 50,000 or at least 55,000 different (i.e., non-identical) probes.

In one embodiment, the microarray is an array (i.e., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50% of the genes in the genome of an organism. Alternatively, the microarrays of the invention can have binding sites for the products encoded by at least 50%, at least 75%, at least 85%, at least 90%, at least 95%, at least 99% or 100% of the genes in the genome of an organism. In other embodiments, the microarrays of the invention can having binding sites for products encoded by fewer than 50%, by at least 50%, by at least 75%, by at least 85%, by at least 90%, by at least 95%, by at least 99% or by 100% of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different coding sequence segments of the gene or an exon of the gene. Such polynucleotides are preferably of the length of 15 to 200 bases, more preferably of the length of 20 to 100 bases, most preferably 40-60 bases. It will be understood that each probe sequence may also comprise linker sequences in addition to the sequence that is complementary to its target sequence. As used herein, a linker sequence refers to a sequence between the sequence that is complementary to its target sequence and the surface of support. For example, in preferred embodiments the profiling arrays of the invention comprise one probe specific to each target gene or exon. However, if desired, the profiling arrays may contain at least 2, 5, 10, 100, 1000 probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such set of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In a preferred embodiment, the probe set contains variant junction probes specifically hybridizable to each of all different splice junction sequences of the exon. In another preferred embodiment, the probe set contains exon specific probes specifically hybridizable to the common sequences in all different variants of the exon, and/or variant junction probes specifically hybridizable to the different splice junction sequences of the exon.

In some other embodiments of the invention, an exon is represented in the exon profiling arrays by a probe comprising a polynucleotide that is complementary to the full length exon. In such embodiments, an exon is represented by a single binding site on the profiling arrays. In some preferred embodiments of the invention, an exon is represented by one or more binding sites on the profiling arrays, each of the binding sites comprising a probe with a polynucleotide sequence that is complementary to an RNA fragment that is a substantial portion of the target exon. The lengths of such probes are normally between about 15-600 bases, preferably between about 20-200 bases, more preferably between about 30-100 bases, and most preferably between about 40-80 bases. The average length of an exon is about 200 bases (see, e.g., Lewin, *Genes V*, Oxford University Press, Oxford, 1994). A probe of length of about 40-80 allows more specific binding of the exon than a probe of shorter length, thereby increasing the specificity of the probe to the target exon. For certain genes, one or more targeted exons may have sequence lengths less than about 40-80 bases. In such cases, if probes with sequences longer than the target exons are to be used, it may be desirable to design probes comprising sequences that include the entire target exon flanked by sequences from the adjacent constitutively splice exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequence used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some other embodiments of the invention, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exons so that cross hybridization can be minimized. Probes that comprise sequences from more than one exons are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one skilled in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5' untranslated region ("UTR"), introns, exons and a 3' UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer the 99 amino acid residues in length. Analysis of these ORFs indicates that there are 5,885 ORFs that are likely to encode protein products (Goffeau et al., 1996, *Science* 274:546-567). In contrast, the human genome is estimated to contain approximately 30,000 to 130,000 genes (see Crollius et al., 2000, *Nature Genetics* 25:235-238; Ewing et al., 2000, *Nature Genetics* 25:232-234). Genome sequences for other organisms, including but not limited to Drosophila, *C. elegans*, plants, e.g., rice and Arabidopsis, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, change the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5'carboxy-fluorescein ("FMA"), 2', 7'-dimethoxy-4', 5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from 0 to in excess of what is required for sampling of the bound polynucleotides (i.e., the probe or probes) by the labeled polynucleotides so that the mixture is close to or substantially reached equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at about 2, 4, 6, 10, 12, 16, 18, 48 or 72 times as long as the first hybridization time.

5.6.2. Preparing Probes for Microarrays

As noted above, the "probe" to which a particular polynucleotide molecule, such an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than about 40 bases in length. Alternatively, when a large set of redundant probes is to be used for an exon, the probes normally comprise nucleotide sequences of about 40-60 bases. The probes can also comprise sequences complementary to full length exons. The lengths of exons can range from less than 50 bases to more than 200 bases. Therefore, when a probe length longer than exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes may comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (i.e., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between about 15 and about 600 bases in length, more typically between about 20 and about 100 bases, most preferably between about 40 and about 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 365:566-568; U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-216).

5.6.3. Attaching Probes to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al, 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Pease et al., 1994, *Proc. Natl. Acad. Sci. U.S.A.* 91:5022-5026; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 pL or less, more preferably 50 pL or less) and are separated from each other on the microarray (e.g., by hydrophobic domains) to form circular surface tension wells which define the locations of the array elements (i.e., the different probes). Polynucleotide probes are normally attached to the surface covalently at the 3' end of the polynucleotide. Alternatively, polynucleotide probes can be attached to the surface covalently at the 5' end of the polynucleotide (see for example, Blanchard, 1998, in *Synthetic DNA Arrays in Genetic Engineering*, Vol. 20, J. K. Setlow, Ed., Plenum Press, New York at pages 111-123).

5.6.4. Target Polynucleotide Molecules

Target polynucleotides which may be analyzed by the methods and compositions of the invention include RNA molecules such as, but by no means limited to messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides may be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, fraction thereof) and messenger RNA is purified from the total extracted RNA. Methods for preparing total and poly(A)$^+$ RNA are well known in the art, and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636, 5,716,785; 5,545,522 and 6,132,997; see also, U.S. patent application Ser. No. 09/411,074, filed Oct. 4, 1999 by Linsley and Schelter and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{14}$C, $^{15}$N and $^{125}$I. Fluorescent molecules suitable for the present invention include, but are not limited to, fluorescein and its derivatives, rhodamine and its derivatives, texas red, 5'carboxy-fluorescein ("FMA"), 2', 7'-dimethoxy-4', 5'-dichloro-6-carboxy-fluorescein ("JOE"), N,N,N',N'-tetramethyl-6-carboxy-rhodamine ("TAMRA"), 6'carboxy-X-rhodamine ("ROX"), HEX, TET, IRD40, and IRD41. Fluroescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.6.5. Hybridization to Microarrays

As described supra, nucleic acid hybridization and wash conditions are chosen so that the polynucleotide molecules to be analyzed by the invention (referred to herein as the "target polynucleotide molecules") specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Shena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, *Nonisotopic DNA Probe Techniques*, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30% formamide.

5.6.6. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced by from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exons expressed in the mRNA will decrease.

The use of a two-color fluorescence labeling and detection scheme to define alterations in gene expression has been described in connection with detection of mRNAs, e.g., in Shena et al., 1995, Quantitative monitoring of gene expression patterns with a complementary DNA microarray, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

In other preferred embodiments, single-channel detection methods, e.g., using one-color fluorescence labeling, are used (see U.S. provisional patent application Ser. No. 60/227,966, filed on Aug. 25, 2000). In this embodiment, arrays comprising reverse-complement (RC) probes are designed and produced. Because a reverse complement of a DNA sequence has sequence complexity that is equivalent to the corresponding forward-strand (FS) probe that is complementary to a target sequence with respect to a variety of measures (e.g., measures such as GC content and GC trend are invariant under the reverse complement), a RC probe is used to as a control probe for determination of level of non-specific cross hybridization to the corresponding FS probe. The significance of the FS probe intensity of a target sequence is determined by comparing the raw intensity measurement for the FS probe and the corresponding raw intensity measurement for the RC probe in conjunction with the respective measurement errors. In a preferred embodiment, an exon is called present if the intensity difference between the FS probe and the corresponding RC probe is significant. More preferably, an exon is called present if the FS probe intensity is also significantly above background level. Single-channel detection methods can be used in conjunction with multi-color labeling. In one embodiment, a plurality of different samples, each labeled with a different color, is hybridized to an array. Differences between FS and RC probes for each color are used to determine the level of hybridization of the corresponding sample.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors may be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of about 25% (i.e., RNA is 25% more abundant in one source than in the other source), more usually about 50%, even more often by a factor of about 2 (i.e., twice as abundant), 3 (three times as abundant), or 5 (five times as abundant) is scored as a perturbation. Present detection methods allow reliable detection of difference of an order of about 3-fold to about 5-fold, but more sensitive methods are expected to be developed.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.6.7. Other Methods of Transcriptional State Measurement

The transcriptional state of a cell may be measured by other gene expression technologies known in the art. Several such technologies produce pools of restriction fragments of limited complexity for electrophoretic analysis, such as methods combining double restriction enzyme digestion with phasing primers (see, e.g., European Patent O 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

5.7. Measurement of other Aspects of the Biological State

In various embodiments of the present invention, aspects of the biological state other than the transcriptional state, such as the translational state, the activity state, or mixed aspects can be measured to produce the measured data to be analyzed according to the invention. Thus, in such embodiments, gene expression data may include translational state measurements or even protein expression measurements. In fact, in some embodiments, rather than using gene expression interaction maps based on gene expression, protein expression interaction maps based on protein expression maps are used. Details of embodiments in which aspects of the biological state other than the transcriptional state are described in this section.

5.7.1. Embodiments Based on Translational State Measurements

Measurement of the translational state may be performed according to several methods. For example, whole genome monitoring of protein (i.e., the "proteome," Goffeau et al., 1996, *Science* 274:546-567; Gygi et al., 1999, Nature Biotechnology 17:994-999) can be carried out by constructing a microarray in which binding sites comprise immobilized, preferably monoclonal, antibodies specific to a plurality of protein species encoded by the cell genome (see, e.g., au et al., 2001, Science 293:2101-2105; MacBeath et al., 2000, Science 289:1760-63; de Wildt et al., 2000, Nature Biotechnology 18:989-994). Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In a preferred embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated and measured by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins. A Practical Approach*, IRL Press, New York; Shevchenko et al., 1996, *Proc. Natl. Acad. Sci. USA* 93:1440-1445; Sagliocco et al., 1996, *Yeast* 12:1519-1533; Lander, 1996, *Science* 274:536-539; and Beaumont et al., Life Science News 7, 2001, Amersham Pharmacia Biotech. The resulting electropherograms can be analyzed by numerous techniques, including mass spectrometric techniques, Western blotting and immunoblot analysis using polyclonal and monoclonal antibodies, and internal and N-terminal microsequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.7.2. Embodiments Based on other Aspects of the Biological State

Even though methods of this invention are illustrated by embodiments involving gene expression, the methods of the invention are applicable to any cellular constituent that can be monitored. In particular, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In alternative and non-limiting embodiments, response data may be formed of mixed aspects of the biological state of a cell. Response data can be constructed from, e.g., changes in certain mRNA abundances, changes in certain protein abundances, and changes in certain protein activities.

5.8. Measurement of Drug Response Date

Drug responses are obtained for use in the instant invention by measuring the gene expression state changed by drug exposure. The biological response described on the exon level can also be measured by exon profiling methods. The measured response data include values representing gene expression level values or gene expression level ratios for a plurality of genes.

To measure drug response data, cell can be exposed to graded levels of the drug or drug candidate of interest. When the cells are grown in vitro, the compound is usually added to their nutrient medium. The drug is added in a graded amount that depends on the particular characteristics of the drug, but usually will be between about 1 ng/ml and 100 mg/ml. In some cases a drug will be solubilized in a solvent such as DMSO.

The exon expression profiles of cells exposed to the drug and of cells not exposed to the drug are measured according to the methods described in the previous section. Preferably, gene transcript arrays are used to find the genes with altered gene expression profiles due to exposure to the drug.

It is preferable for measurements of drug responses, in the case of two-colored differential hybridization described above, to measure with reversed labeling. Also, it is preferable that the levels of drug exposure used provide sufficient resolution of rapidly changing regions of the drug response, e.g., by using approximately ten levels of drug exposure.

5.9. Methods for Probing Biological States

One aspect of the invention provides methods for the analysis of biological state. The methods of this invention are also useful for the analysis of responses of a cell sample to perturbations designed to probe cellular state. Preferred perturbations are those that cause a change in the amount of alternative splicing that occurs in one or more RNA transcripts. This section provides some illustrative methods for probing gene expression states and protein abundances and acitivities. See PCT publication WO 00/24936 for more detailed descriptions of these method.

Methods for targeted perturbation of cells are widely known and applied in the art. For example, such methods include use of titratable expression systems, use of transfection or viral transduction systems, direct modifications to RNA abundances or activities, direct modifications of protein abundances, direct modification of protein activities including use of drugs (or chemical moieties in general), and post-transcriptional gene silencing (PTGS) or RNA interference (RNAi).

In mammalian cells, several means of titrating expression of genes are available (Spencer, 1996, Trends Genet. 12:181-187). For example, the Tet system is widely used, both in its original form, the "forward" system, in which addition of doxycycline represses transcription, and in the newer "reverse" system, in which doxycycline addition stimulates transcription (Gossen et al., 1992, Proc. Natl. Acad. Sci. USA 89:5547-5551; Hoffmann et al., 1997, Nucl. Acids. Res. 25:1078-1079; Hofmann et al., 1996, Proc. Natl. Acad. Sci. USA 93:5185-5190; Paulus et al., 1996, Journal of Virology 70:62-67). Another commonly used controllable promoter system in mammalian cells is the ecdysone-inducible system developed by Evans and colleagues (No et al., 1996, Proc. Nat. Acad. Sci. USA 93:3346-3351), where expression is controlled by the level of muristerone added to the cultured cells. Finally, expression can be modulated using the "chemical-induced dimerization" (CID) system developed by Schreiber, Crabtree, and colleagues (Belshaw et al., 1996, Proc. Nat. Acad. Sci. USA 93:4604-4607; Spencer, 1996, Trends Genet. 12:181-187) and similar systems in yeast. In this system, the gene of interest is put under the control of the CID-responsive promoter, and transfected into cells expressing two different hybrid proteins, one comprised of a DNA-binding domain fused to FKBP12, which binds FK506. The other hybrid protein contains a transcriptional activation domain also fused to FKBP12. The CID inducing molecule is FK1012, a homodimeric version of FK506 that is able to bind simultaneously both the DNA binding and transcriptional activating hybrid proteins. In the graded presence of FK1012, graded transcription of the controlled gene is activated.

Transfection or viral transduction of target genes can introduce controllable perturbations in biological gene expression states in mammalian cells. Preferably, transfection or transduction of a target gene can be used with cells that do not naturally express the target gene of interest. Such non-expressing cells can be derived from a tissue not normally expressing the target gene or the target gene can be specifically mutated in the cell. The target gene of interest can be cloned into one of many mammalian expression plasmids, for example, the pcDNA3.1+/−system (Invitrogen, Inc.) or retroviral vectors, and introduced into the non-expressing host cells. Transfected or transduced cells expressing the target gene may be isolated by selection for a drug resistance marker encoded by the expression vector. The level of gene transcription is monotonically related to the transfection dosage. In this way, the effects of varying levels of the target gene may be investigated. Other methods of modifying RNA abundances and activities and thus gene abundances include ribozymes, antisense species, and RNA aptamers (Good et al., 1997, Gene Therapy 4: 45-54). Controllable application or exposure of a cell to these entities permits controllable perturbation of RNA abundances.

Ribozymes are RNAs which are capable of catalyzing RNA cleavage reactions. (Cech, 1987, Science 236:1532-1539; PCT International Publication WO 90/11364, published Oct. 4, 1990; Sarver et al., 1990, Science 247: 1222-1225). "Hairpin" and "hammerhead" RNA ribozymes can be designed to specifically cleave a particular target mRNA. Rules have been established for the design of short RNA molecules with ribozyme activity, which are capable of cleaving other RNA molecules in a highly sequence specific way and can be targeted to virtually all kinds of RNA. (Haseloff et al., 1988, Nature 334:585-591; Koizumi et al., 1988, FEBS Lett., 228:228-230; Koizumi et al., 1988, FEBS Lett., 239: 285-288). Ribozyme methods involve exposing a cell to, inducing expression in a cell, etc. of such small RNA ribozyme molecules. (Grassi and Marini, 1996, Annals of Medicine 28: 499-510; Gibson, 1996, Cancer and Metastasis Reviews 15: 287-299).

In another embodiment, activity of a target RNA (preferable mRNA) species, specifically its rate of translation, can be controllably inhibited by the controllable application of antisense nucleic acids. An "antisense" nucleic acid as used herein refers to a nucleic acid capable of hybridizing to a sequence-specific (e.g., non-poly A) portion of the target RNA, for example its translation initiation region, by virtue of some sequence complementarity to a coding and/or non-coding region. The antisense nucleic acids of the invention can be oligonucleotides that are double-stranded or single-stranded, RNA or DNA or a modification or derivative thereof, which can be directly administered in a controllable manner to a cell or which can be produced intracellularly by transcription of exogenous, introduced sequences in controllable quantities sufficient to perturb translation of the target RNA.

In still another embodiment, RNA aptamers can be introduced into or expressed in a cell. RNA aptamers are specific RNA ligands for proteins, such as for Tat and Rev RNA (Good et al., 1997, Gene Therapy 4: 45-54) that can specifically inhibit their translation.

Post-transcriptional gene silencing (PTGS) or RNA interference (RNAi) can also be used to modify RNA abundances (Guo et al., 1995, Cell 81:611-620; Fire et al., 1998, Nature 391: 806-811). In RNAi, dsRNAs are injected into cells to specifically block expression of its homologous gene. In particular, in RNAi, both the sense strand and the anti-sense strand can inactivate the corresponding gene. It is suggested that the dsRNAs are cut by nuclease into 21-23 nucleotide fragments. These fragments hybridize to the homologous region of their corresponding mRNAs to form double-stranded segments which are degraded by nuclease (Grant, 1999, Cell 96:303-306; Tabara et al., 1999, Cell 99:123-132; Zamore et al., 2000, Cell 101:25-33; Bass, 2000, Cell 101: 235-238; Petcherski et al., 2000, Nature 405:364-368; Elbashir et al., Nature 411:494-498; Paddison et al., Proc. Natl. Acad. Sci. USA 99:1443-1448; Technical Bulletins at the Dharmacon, Inc. web site). Therefore, in one embodiment, one or more dsRNAs having sequences homologous to the sequences of one or more mRNAs whose abundances are to be modified are transfected into a cell or tissue sample. Any standard method for introducing nucleic acids into cells can be used.

Methods of modifying protein abundances include, inter alia, those altering protein degradation rates and those using antibodies (which bind to proteins affecting abundances of activities of native target protein species). Increasing (or decreasing) the degradation rates of a protein species decreases (or increases) the abundance of that species. Methods for controllably increasing the degradation rate of a target protein in response to elevated temperature and/or exposure to a particular drug, which are known in the art, can be employed in this invention. For example, one such method employs a heat-inducible or drug-inducible N-terminal degron, which is an N-terminal protein fragment that exposes a degradation signal promoting rapid protein degradation at a higher temperature (e.g., 37° C.) and which is hidden to prevent rapid degradation at a lower temperature (e.g., 23° C.) (Dohmen et. al, 1994, Science 263:1273-1276). Such an exemplary degron is Arg-DHFR$^{ts}$, a variant of murine dihydrofolate reductase in which the N-terminal Val is replaced by Arg and the Pro at position 66 is replaced with Leu. According to this method, for example, a gene for a target protein, P, is replaced by standard gene targeting methods known in the art (Lodish et al., 1995, *Molecular Biology of the Cell*, W. H.-Freeman and Co., New York, especially chap 8) with a gene coding for the fusion protein Ub-Arg-DHFR$^{ts}$-P ("Ub" stands for ubiquitin). The N-terminal ubiquitin is rapidly cleaved after translation exposing the N-terminal degron. At lower temperatures, lysines internal to Arg-DHFR$^{ts}$ are not exposed, ubiquitination of the fusion protein does not occur, degradation is slow, and active target protein levels are high. At higher temperatures (in the absence of methotrexate), lysines internal to Arg-DHFR$^{ts}$ are exposed, ubiquitination of the fusion protein occurs, degradation is rapid, and active target protein levels are low. Heat activation of degradation is controllably blocked by exposure methotrexate. This method is adaptable to other N-terminal degrees which are responsive to other inducing factors, such as drugs and temperature changes.

Methods of directly modifying protein activities include, inter alia, dominant negative mutations, specific drugs or chemical moieties generally, and also the use of antibodies.

6. EXAMPLE

Test Results

The following example is presented by way of illustration of the present invention, and is not intended to limit the present invention in any way.

To illustrate the difference between the improved ANOVA method of the invention as described in Table 2 and the traditional ANOVA as described in Table 1, two experiments were carried out to compare the false positive rate and the sensitivity in gene differential expression detection between the improved and traditional ANOVA. Affymetrix HG-U95A microarrays are used for all measurements.

To compare false positive rate, five (N=5) replicate microarray measurements were chosen and grouped into three groups (k=3). All five microarrays were hybridized with cell-293, human embryonic kidney cell (Sample A). Two of the groups have two replicates each and one group has only one replicate. Because all five replicates are measurements of sample A, none of the genes or probes measured should be detected as differentially expressed. Thus, in this experiment, any gene or probes determined as being differentially expressed are false positives. The false positive rate is the number of false positives divided by the total number of gene or probes in the microarray. The lower the false positive rate, the better the method.

To compare the detection sensitivity, another five microarrays were selected and grouped into three groups (k=3). Two of the groups, having two and one replicate, repectively, contains measurements obtained using Sample A. The third group has two replicates that are obtained using cell-A549, human lung cancer cell (Sample B). Sample A and Sample B are very different, and therefore, differential expressions between the two different samples are expected. In this case, the detection sensitivity is evaluated based on the rate of detection, which is the number of genes or probes detected as differentially expressed divided by the total number of genes or probes in the microarray. The higher the detection rate, the more sensitive the method.

Table 5 summarizes the test results. For the given threshold p-value<0.01, the improved ANOVA method provides both much lower false positive rate and much higher detection sensitivity. This indicates that the improved ANOVA method of the invention with two inputs has higher statistical power than the traditional ANOVA.

TABLE 5

| Test Results (P-value < 0.01) | | |
|---|---|---|
| Analysis methods | False Positive rate | Detection rate |
| Textbook ANOVA | 0.0093 | 0.17 |
| Improved ANOVA | 0.00048 | 0.30 |

7. REFERENCES CITED

All references cited herein are incorporated herein by reference in their entirety and for all purposes to the same extent as if each individual publication or patent or patent application was specifically and individually indicated to be incorporated by reference in its entirety for all purposes.

Many modifications and variations of the present invention can be made without departing from its spirit and scope, as will be apparent to those skilled in the art. The specific embodiments described herein are offered by way of example only, and the invention is to be limited only by the terms of the appended claims along with the full scope of equivalents to which such claims are entitled.

What is claimed is:

1. A method of analyzing a plurality of measurements of a biological variable $\{y_{ti}\}$ in k different measurement groups by ANOVA analysis to determine whether there are differences among said k different measurement groups, wherein the biological variable is a transcript level of a gene measured using a microarray or an abundance of a protein measured using a protein microarray or two-dimensional gel electrophoresis, wherein $y_{ti}$ is the ith measurement in the tth measurement group, $t=1, 2, \ldots, k$ and $i=1, 2, \ldots, n_t$, $n_t$ being the number of measurements in the tth measurement group, wherein each said measurement group consists of $n_t$ measurements of said biological variable under a condition common to said measurement group, and wherein each said measurement $y_{ti}$ has a predetermined measurement variance $\sigma_{ti}^2$, said method comprising on a computer receiving, by the computer, data representing the plurality of measurements of a biological variable $\{y_{ti}\}$ in k different measurement groups;

determining, by the computer, the predetermined measurement variance $\sigma_{ti}^2$, wherein said predetermined measurement variance $\sigma_{ti}^2$ of each said measurement $y_{ti}$ is determined according to an error model, wherein said error model is a three-term error model according to equation $$\sigma_{ti}^2 = c^2 + b^2 \cdot y_{ti} + a^2 \cdot y_{ti}^2$$

wherein a is a fractional error coefficient, b is a Poisson error coefficient, and c is a standard deviation of background noise, the predetermined measurement variance being based on prior measurements of the same biological variable using the same microarray or two-dimensional gel electrophoresis;

(a) determining, by the computer, a within-group variance for said k different measurement groups, wherein said within-group variance consists of a propagated variance and a scattered variance, said propagated variance being determined based on said predetermined measurement variances $\{\sigma_{ti}^2\}$ of said plurality of measurements $\{y_{ti}\}$, and said scattered variance being determined based on deviations of said measurements in said plurality of measurements with respect to their respective group means $\{\bar{y}_t\}$, wherein each said group mean $\bar{y}_t$ is the mean of said $n_t$ measurements in said tth measurement group, wherein said within-group variance is determined based on group variances $\{\sigma_{\bar{y}_t}^2\}$ of said k different measurement groups, said group variance $\sigma_{\bar{y}_t}^2$ for said tth measurement group consisting of a measurement group propagated variance $\sigma_{\bar{y}_tP}^2$ and a measurement group scattered variance $\sigma_{\bar{y}_tS}^2$, wherein said measurement group propagated variance $\sigma_{\bar{y}_tP}^2$ is determined according to the equation $$\sigma_{\bar{y}_tP}^2 = \frac{\sum_{i=1}^{n_t} \sigma_{ti}^2}{n_t^2}$$

and wherein said measurement group scattered variance $\sigma_{\bar{y}_tS}^2$ is determined according to the equation $$\sigma_{\bar{y}_tS}^2 = \frac{1}{(n_t-1)} \cdot \sum_{i=1}^{n_t} (y_{ti} - \bar{y}_t)^2;$$

(b) determining, by the computer, a between-group variance for said k different measurement groups, wherein said between-group variance is a variance of said group means $\{\bar{y}_t\}$ with respect to a mean of said plurality of measurements $\{y_{ti}\}$;

(c) comparing, by the computer, said within-group variance with said between-group variance to determine a result representing whether there are any differences there between; and (d) outputting to a user, a user interface device, a computer readable storage medium, or a local or remote computer system; or displaying: the result of said comparing step (c) in order to provide the result of the analysis of the plurality of measurements of the biological variable, which is a transcript level of a gene measured using a microarray or an abundance of a protein measured using a protein microarray or two-dimensional gel electrophoresis;

wherein said predetermined measurement variances $\{\sigma_{ti}^2\}$ are determined prior to said steps (a)-(d); thereby determining whether there are differences among said k different measurement groups.

2. The method of claim 1, wherein said group propagated variance and said group scattered variance are combined according to the equation $$\sigma_{\bar{y}_t} = \frac{\sigma_{\bar{y}_tP} + (n_t-1) \cdot \sigma_{\bar{y}_tS}}{n_t}.$$

3. The method of claim 2, wherein said comparing step comprises determining the significance level of a statistical metric by a statistical test, wherein said statistical metric is determined by a method comprising (i) determining a within-group degree of freedom;
(ii) determining a between-group degree of freedom;
(iii) determining a within-group mean square;
(iv) determining a between-group mean square; and
(v) calculating said statistical metric.

4. The method of claim 3, wherein said within-group degree of freedom is calculated according to the equation $$v_R = N - k + \sum_{t=1}^{k} \frac{1}{n_t}$$

where $v_R$ is said within-group degree of freedom, said between-group degree of freedom is calculated according to the equation $$v_T = k - 1$$

where $v_T$ is said between-group degree of freedom, said within-group mean square is calculated according to the equation $$s_R^2 = S_R/v_R$$

where $S_R^2$ is said within-group mean square and where $S_R$ is calculated according to the equation $$S_R = \sum_{t=1}^{k}\left[v_{Rt} \cdot \frac{(\sigma_{\bar{y}_t,P} + (n_t - 1) \cdot \sigma_{\bar{y}_t,s})^2}{n_t}\right]$$

where $v_{Rt}$ is calculated according to the equation $$v_{Rt} = n_t - 1 + \frac{1}{n_t}$$

and said between-group mean square is calculated according to the equation $$s_T^2 = S_T/v_T$$

where $s_T^2$ is said between-group mean square and where $S_T$ is calculated according to the equation $$S_T = \sum_{t=1}^{k} n_t \cdot (\bar{y}_t - \bar{y})^2$$

where $\bar{y}$ is calculated according to the equation $$\bar{y} = \frac{\sum_{t=1}^{k}\sum_{i=1}^{n_t} y_{ti}}{N}$$

where N is the total number of measurements.

5. The method of claim 4, wherein said statistical test is an F-test and said significance level is a p-value determined according to the equation $$p\text{value} = 1 - fcdf(s_T^2/s_R^2, v_T, v_R).$$

6. The method of claim 5, wherein said variable is the transcript level of a gene.

7. The method of claim 6, wherein said transcript level is measured using a DNA microarray.

8. The method of claim 7, wherein said variable is the abundance of a protein.

9. The method of claim 8, wherein said abundance is measured using a protein microarray.

10. The method of claim 8, wherein said abundance is measured using two-dimensional gel electrophoresis.

11. A method for analyzing variation among a plurality of measurements of a biological variable $\{y_t\}$ to determine whether there are differences among said plurality of measurements, wherein the biological variable is a transcript level of a gene measured using a microarray or an abundance of a protein measured using a protein microarray or two-dimensional gel electrophoresis, wherein $y_t$ is the tth measurement, t=1, 2, . . . , $n_t$, $n_t$ being the number of measurements, wherein said plurality of measurements are measured under a common condition, wherein each said measurement has a predetermined measurement variance $\sigma_t^2$, said method comprising on a computer receiving, by the computer, data representing the predetermined measurement variance $\sigma_t^2$, the predetermined measurement variance being based on prior measurements of the same biological variable, determining, by the computer, an error-weighted measurement for each measurement in said plurality of measurements by weighting each measurement in said plurality of measurements with a weighting factor, wherein said weighting factor is determined based on said predetermined measurement variance of said measurement;

(a) determining, by the computer, a propagated variance and a scattered variance, wherein said propagated variance is determined based on said predetermined measurement variances $\{\sigma_t^2\}$ of said plurality of measurements $\{y_t\}$ and wherein said scattered variance is a variance of said plurality of measurements with respect to the mean $\bar{y}$ of said plurality of measurements;

(b) comparing, by the computer, said propagated variance and said scattered variance, thereby determining whether there are differences among said plurality of measurements; and (c) outputting to a user, a user interface device, a computer readable storage medium, or a local or remote computer system; or displaying: a result of said comparing step (b) in order to provide the result of the analysis of the plurality of measurements of the biological variable, which is a transcript level of a gene measured using a microarray or an abundance of a protein measured using a protein microarray or two-dimensional gel electrophoresis;

wherein said predetermined measurement variances $\{\sigma_t^2\}$ are determined prior to said steps (a)-(c).

12. The method of claim 11, wherein said weighting factor is determined according to the equation $$w_{ti} = \frac{1}{\sigma_{ti}^2}$$

where $\sigma_t^2$ is said predetermined measurement variance of measurement $y_t$.

13. The method of claim 11, wherein said comparing is carried out using an F-test according to the equation Consistency_$p$value=$1 - fcdf(\sigma_{y_s}^2/\sigma_{\bar{y}_t,P}^2, n_t-1, n_t)$.

14. A computer system comprising
a processor, and
a memory coupled to said processor and encoding one or more programs,
wherein said one or more programs cause the processor to carry out a method of analyzing a plurality of measurements of a biological variable $\{y_{ti}\}$ in k different measurement groups by ANOVA analysis to determine whether there are differences among said k different measurement groups, wherein $y_{ti}$ is the ith measurement in the tth measurement group, t=1, 2, . . . , k and i=1, 2, . . . , $n_t$, $n_t$ being the number of measurements in the tth measurement group, wherein each said measurement group consists of $n_t$ measurements of said biological variable under a condition common to said measurement group, and wherein each said measurement $y_{ti}$ has a predetermined measurement variance $\sigma_{ti}^2$, said method comprising determining the predetermined measurement variance $\sigma_{ti}^2$, wherein said predetermined measurement variance $\sigma_{ti}^2$ of each said measurement $y_{ti}$ is determined according to an error model, wherein said error model is a three-term error model according to equation $$\sigma_{ti}^2 = c^2 + b^2 \cdot y_{ti} + a^2 \cdot y_{ti}^2$$

wherein a is a fractional error coefficient, b is a Poisson error coefficient, and c is a standard deviation of background noise (a) determining a within-group variance for said k different measurement groups, wherein said within-group variance consists of a propagated variance and a scattered variance, said propagated variance being determined based on said predetermined measurement variances $\{\sigma_{ti}^2\}$ of said plurality of measurements $\{y_{ti}\}$, the predetermined measurement variances being based on prior measurements of the same biological variable using the same microarray or two-dimensional gel electrophoresis, and said scattered variance being determined based on deviations of said measurements in said plurality of measurements with respect to their respective group means $\{\bar{y}_t\}$, wherein each said group mean $\bar{y}_t$ is the mean of said $n_t$ measurements in said tth measurement group;

(b) determining a between-group variance for said k different measurement groups, wherein said between-group variance is a variance of said group means $\{\bar{y}_t\}$ with respect to a mean of said plurality of measurements $\{y_{ti}\}$;

(c) comparing said within-group variance with said between-group variance; and (d) outputting to a user, a user interface device, a computer readable storage medium, or a local or remote computer system; or displaying: a result of said comparing step (c);

wherein said predetermined measurement variances $\{\sigma_{ti}^2\}$ are determined prior to said steps (a)-(d); thereby determining whether there are differences among said k different measurement groups and wherein said propagated variance is determined according to the equation $$\sigma_{\bar{y}_t P}^2 = \frac{\sum_{i=1}^{n_t} \sigma_{ti}^2}{n_t^2}$$

and wherein said scattered variance is determined according to the equation $$\sigma_{\bar{y}_t S}^2 = \frac{1}{(n_t - 1)} \cdot \sum_{i=1}^{n_t} (y_{ti} - \bar{y}_t)^2.$$

15. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method of analyzing a plurality of measurements of a biological variable $\{y_{ti}\}$ in k different measurement groups by ANOVA analysis to determine whether there are differences among said k different measurement groups, wherein $y_{ti}$ is the ith measurement in the tth measurement group, $t=1, 2, \ldots, k$ and $i=1, 2, \ldots, n_t$, $n_t$ being the number of measurements in the tth measurement group, wherein each said measurement group consists of $n_t$ measurements of said biological variable under a condition common to said measurement group, and wherein each said measurement $y_{ti}$ has a predetermined measurement variance $\sigma_{ti}^2$, said method comprising receiving, on a computer, data representing the plurality of measurements of a biological variable $\{y_{ti}\}$ in k different measurement groups;

determining the predetermined measurement variance $\sigma_{ti}^2$, wherein said predetermined measurement variance $\sigma_{ti}^2$ of each said measurement $y_{ti}$ is determined according to an error model based on a fractional error coefficient, a Poisson error coefficient, and a standard deviation of background noise, the predetermined measurement variance being based on prior measurements of the same biological variable using the same microarray or two-dimensional gel electrophoresis;

(a) determining a within-group variance for said k different measurement groups, wherein said within-group variance consists of a propagated variance and a scattered variance, said propagated variance being determined based on said predetermined measurement variances $\sigma_{ti}^2$ of said plurality of measurements $\{y_{ti}\}$, and said scattered variance being determined based on deviations of said measurements in said plurality of measurements with respect to their respective group means $\{\bar{y}_t\}$ wherein each said group mean $\bar{y}_t$ is the mean of said $n_t$ measurements in said tth measurement group, wherein said within-group variance is determined based on group variances $\{\sigma_{\bar{y}_t}^2\}$ of said k different measurement groups, said group variance $\sigma_{\bar{y}_t}^2$ for said tth measurement group consisting of a measurement group propagated variance $\sigma_{\bar{y}_t P}^2$ and a measurement group scattered variance $\sigma_{\bar{y}_t S}^2$, wherein said measurement group propagated variance $\sigma_{\bar{y}_t P}^2$ is determined according to the equation $$\sigma_{\bar{y}_t P}^2 = \frac{\sum_{i=1}^{n_t} \sigma_{ti}^2}{n_t^2}$$

and wherein said measurement group scattered variance $\sigma_{\bar{y}_t S}^2$ is determined according to the equation $$\sigma_{\bar{y}_t S}^2 = \frac{1}{(n_t - 1)} \cdot \sum_{i=1}^{n_t} (y_{ti} - \bar{y}_t)^2;$$

(b) determining a between-group variance for said k different measurement groups, wherein said between-group variance is a variance of said group means $\{\bar{y}_t\}$ with respect to a mean of said plurality of measurements $\{y_{ti}\}$;

(c) comparing said within-group variance with said between-group variance; and (d) outputting to a user, a user interface device, a computer readable storage medium, or a local or remote computer system; or displaying: a result of said comparing step (c) in order to provide the result of the analysis of the plurality of measurements of the biological variable, which is a transcript level of a gene measured using a microarray or an abundance of a protein measured using a protein microarray or two-dimensional gel electrophoresis;

wherein said predetermined measurement variances $\sigma_{ti}^2$ are determined prior to said steps (a)-(d); thereby determining whether there are differences among said k different measurement groups.

16. A computer system comprising
a processor, and
a memory coupled to said processor and encoding one or more programs,
wherein said one or more programs cause the processor to carry out a method for analyzing variation among a plurality of measurements of a biological variable $\{y_t\}$ to determine whether there are differences among said plurality of measurements, wherein $y_t$ is the tth measurement, $t=1, 2, \ldots, n_t$, $n_t$ being the number of measurements, wherein said plurality of measurements are measured under a common condition, wherein each said measurement has a predetermined measurement variance $\sigma_t^2$, said method comprising
(a) determining a propagated variance based on said predetermined measurement variances $\{\sigma_t^2\}$ of said plurality of measurements $\{y_t\}$, wherein said propagated variance is determined according to the equation $$\sigma_{y_t p}^2 = \frac{\sum_{i=1}^{n_t} \sigma_t^2}{n_t^2};$$

wherein the predetermined measurement variances are based on prior measurements of the same biological variable using the same microarray or two-dimensional gel electrophoresis; and
(b) outputting to a user, a user interface device, a computer readable storage medium, or a local or remote computer system; or displaying: a result of said determining step (a) in order to provide the result of the analysis of the plurality of measurements of the biological variable, which is a transcript level of a gene measured using a microarray or an abundance of a protein measured using a protein microarray or two-dimensional gel electrophoresis.

17. A computer program product for use in conjunction with a computer having a processor and a memory connected to the processor, said computer program product comprising a computer readable storage medium having a computer program mechanism encoded thereon, wherein said computer program mechanism may be loaded into the memory of said computer and cause said computer to carry out a method for analyzing variation among a plurality of measurements of a biological variable $\{y_t\}$ to determine whether there are differences among said plurality of measurements, wherein $y_t$ is the tth measurement, $t=1, 2, \ldots, n_t$, $n_t$ being the number of measurements, wherein said plurality of measurements are measured under a common condition, wherein each said measurement has a predetermined measurement variance $\sigma_t^2$, said method comprising
(a) determining a propagated variance based on said predetermined measurement variances $\{\sigma_t^2\}$ of said plurality of measurements $\{y_t\}$ wherein said propagated variance is determined according to the equation $$\sigma_{y_t p}^2 = \frac{\sum_{i=1}^{n_t} \sigma_t^2}{n_t^2},$$

wherein the predetermined measurement variances are based on prior measurements of the same biological variable using the same microarray or two-dimensional gel electrophoresis; and
(b) outputting to a user, a user interface device, a computer readable storage medium, or a local or remote computer system; or displaying: a result of said determining step (a) in order to provide the result of the analysis of the plurality of measurements of the biological variable, which is a transcript level of a gene measured using a microarray or an abundance of a protein measured using a protein microarray or two-dimensional gel electrophoresis.

18. A method for analyzing variation among a plurality of measurements of a biological variable $\{y_t\}$ to determine whether there are differences among said plurality of measurements, wherein the biological variable is a transcript level of a gene measured using a microarray or an abundance of a protein measured using a protein microarray or two-dimensional gel electrophoresis, wherein $y_t$ is the tth measurement, $t=1, 2, \ldots, n_t$, $n_t$ being the number of measurements, wherein said plurality of measurements are measured under a common condition, wherein each said measurement has a predetermined measurement variance $\sigma_t^2$, said method comprising
on a computer
receiving, by the computer, data representing the plurality of measurements of a biological variable $\{y_t\}$;
determining, by the computer, the predetermined measurement variance $\sigma_t^2$, wherein said predetermined measurement variance $\sigma_t^2$ of each said measurement $y_t$ is determined according to an error model based on a fractional error coefficient, a Poisson error coefficient, and a standard deviation of background noise, the predetermined measurement variance being based on prior measurements of the same biological variable using the same microarray or two-dimensional gel electrophoresis;
(a) determining, by the computer, a propagated variance based on said predetermined measurement variances $\{\sigma_t^2\}$ of said plurality of measurements $\{y_t\}$, wherein said propagated variance is determined according to the equation $$\sigma_{y_t p}^2 = \frac{\sum_{i=1}^{n_t} \sigma_t^2}{n_t^2};$$

and
(b) outputting to a user, a user interface device, a computer readable storage medium, or a local or remote computer system; or displaying: a result of said determining step (a) in order to provide the result of the analysis of the plurality of measurements of the biological variable, which is a transcript level of a gene measured using a microarray or an abundance of a protein measured using a protein microarray or two-dimensional gel electrophoresis.

* * * * *